US011427536B2

(12) United States Patent
Miyake et al.

(10) Patent No.: US 11,427,536 B2
(45) Date of Patent: Aug. 30, 2022

(54) PHOTOCATALYST-FREE, LIGHT-INDUCED CARBON-SULFUR CROSS-COUPLING METHODS

(71) Applicant: THE REGENTS OF THE UNIVERSITY OF COLORADO, A BODY CORPORATE, Denver, CO (US)

(72) Inventors: Garret Miyake, Fort Collins, CO (US); Bin Liu, Boulder, CO (US); Chern-Hooi Lim, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 447 days.

(21) Appl. No.: 16/019,914

(22) Filed: Jun. 27, 2018

(65) Prior Publication Data
US 2018/0370911 A1 Dec. 27, 2018

Related U.S. Application Data

(60) Provisional application No. 62/525,402, filed on Jun. 27, 2017.

(51) Int. Cl.
C07C 319/14 (2006.01)
C07D 213/70 (2006.01)
(Continued)

(52) U.S. Cl.
CPC ........... *C07C 319/14* (2013.01); *B01J 19/123* (2013.01); *B01J 19/127* (2013.01); *C07D 213/70* (2013.01);
(Continued)

(58) Field of Classification Search
CPC ............ C07C 2603/50; C07C 2603/24; C07C 319/14–18; C07D 285/22; C07D 213/70;
(Continued)

(56) References Cited

U.S. PATENT DOCUMENTS 3,206,467 A * 9/1965 Reifschneider ....... C07C 319/14
548/182
3,432,542 A * 3/1969 Ransley ................. C08G 75/12
560/154
(Continued)

FOREIGN PATENT DOCUMENTS

CN 104803898 A * 7/2015

OTHER PUBLICATIONS

Jiang et al, "Room-Temperature Arylation of Thiols: Breakthrough with Aryl Chlorides," Angew. Chem. Int. Ed. 2017, vol. 56, pp. 874-879 (Year: 2017).*
(Continued)

*Primary Examiner* — Nicholas A Smith
(74) *Attorney, Agent, or Firm* — Saul Ewing Arnstein & Lehr LLP; Kathryn Doyle; Domingos J. Silva

(57) ABSTRACT

In one aspect, the invention provides a method of promoting a carbon-sulfur bond forming reaction. In certain embodiments, the reaction comprises cross-coupling of a(n) (hetero)aryl halide with a thiol to form the carbon-sulfur bond, wherein the method is promoted by light irradiation in the absence of a photocatalyst. In other embodiments, the cross-coupling reaction can be promoted through visible light irradiation, including sunlight.

13 Claims, 6 Drawing Sheets

(51) Int. Cl.

| | |
|---|---|
| C07D 239/38 | (2006.01) |
| C07D 285/16 | (2006.01) |
| C07D 235/28 | (2006.01) |
| C07D 311/54 | (2006.01) |
| C07D 215/36 | (2006.01) |
| C07D 277/74 | (2006.01) |
| C07D 285/22 | (2006.01) |
| B01J 19/12 | (2006.01) |

(52) U.S. Cl.
CPC ......... *C07D 215/36* (2013.01); *C07D 235/28* (2013.01); *C07D 239/38* (2013.01); *C07D 277/74* (2013.01); *C07D 285/16* (2013.01); *C07D 285/22* (2013.01); *C07D 311/54* (2013.01); *C07C 2603/24* (2017.05); *C07C 2603/50* (2017.05)

(58) Field of Classification Search
CPC .. C07D 239/38; C07D 285/16; C07D 235/28; C07D 311/54; C07D 215/36; C07D 277/74; B10J 19/123; B01J 19/127; B01J 19/123
USPC .................. 204/157.64, 157.7, 157.76–157.8
See application file for complete search history.

(56) References Cited

U.S. PATENT DOCUMENTS

| | | | | |
|---|---|---|---|---|
| 3,661,743 | A * | 5/1972 | Pierce | C07D 331/04 204/157.7 |
| 4,040,921 | A * | 8/1977 | Fields | B01J 19/127 204/157.78 |
| 9,441,084 | B2 * | 9/2016 | Heardon | C08J 11/04 |
| 2014/0221692 | A1 * | 8/2014 | Netemeyer et al. | B01J 19/12 204/157.76 |

OTHER PUBLICATIONS

Hong et al, "Visible-light-promoted synthesis of diaryl sulfides under air," Tetrahedron Letters 58 (2017) pp. 2809-2812 (Year: 2017).*

Alvaro, et al., "Resting state and elementary steps of the coupling of aryl halides with thiols catalyzed by alkylbisphosphine complexes of palladium", J. Am. Chem. Soc., 131(22), 2009, 7858-7868.

Arceo, et al., "Photochemical activity of a key donor-acceptor complex can drive stereoselective catalytic α-alkylation of aldehydes", Nat. Chem., 5, 2013, 750-756.

Arisawa, et al., "Rhodium-catalyzed substitution reaction of aryl fluorides with disulfides: p-orientation in the polyarylthiolation of polyfluorobenzenes", J. Am. Chem. Soc., 130, 2008, 12214-12215.

Bates, et al., "A general method for the formation of aryl-sulfur bonds using copper(I) catalysts", Org. Lett., 4, 2002, 2803-2806.

Beatty, et al., "Photochemical Perfluoroalkylation with Pyridine N-Oxides: Mechanistic Insights and Performance on a Kilogram Scale", J. Chem., 1(3), 2016, 456-472.

Beletskaya, et al., "Transition-metal-catalyzed C—S, C—Se, and C—Te bond formation via cross-coupling and atom-economic addition reactions", V. P. Chem. Rev., 111(3), 2011, 1596-1636.

Bhadra, et al., "Recyclable Heterogeneous Supported Copper-Catalyzed Coupling of Thiols with Aryl Halides: Base-Controlled Differential Arylthiolation of Bromoiodobenzenes", Adv. Synth. Catal., 351, 2009, 2369-2378.

Boateng, et al., "Optimization of 3-(phenylthio)quinolinium compounds against opportunistic fungal pathogens", Eur. J. Med. Chem, 46(5), 2011, 1789-1797.

Boyd, et al., "Sulfur and Its Role in Modern Materials Science", Angew. Chem., Int. Ed., 55, 2016, 15486-15502.

Bunnett, et al., "Arylation of Arenethiolate Ions by the Srn1 Mechanism. A Convenient Synthesis of Diaryl Sulfides.", J. Org. Chem., 39, 1974, 3173-3174.

Candish, et al., "Transition-Metal-Free, Visible-Light-Enabled Decarboxylative Borylation of Aryl N-Hydroxyphthalimide Esters", J. Am. Chem. Soc., 139(22):2017, 7440-7443.

Correa, et al., "Iron-catalyzed S-arylation of thiols with aryl iodides", Angew. Chem. Int. Ed., 47(15), 2008, 2880-2883.

Deng, et al., "CuI-Catalyzed Coupling Reactions of Aryl Iodides and Bromides with Thiols Promoted by Amino Acid Ligands", Synlett., 2004, 1254 1258.

Deng, et al., "Disulfide-Catalyzed Visible-Light-Mediated Oxidative Cleavage of C=C Bonds and Evidence of an Olefin-Disulfide Charge-Transfer Complex", Angew. Chem., Int. Ed., 56(3), 2017, 832-836.

Du, et al., "Strongly Reducing, Visible-Light Organic Photoredox Catalysts as Sustainable Alternatives to Precious Metals", Chemistry 16;23(46): 2017, 10962-10968.

Eichman, et al., "Zinc-mediated palladium-catalyzed formation of carbon-sulfur bonds", J. Org. Chem., 74(10), 2009, 4005-4008.

Feng, et al., "Sulfur Containing Scaffolds in Drugs: Synthesis and Application in Medicinal Chemistry", Curr. Top. Med. Chem., 16(11), 2016, 1200-1216.

Fernandez-Rodriguez, et al., "A general and long-lived catalyst for the palladium-catalyzed coupling of aryl halides with thiols", J. Am. Chem. Soc., 128(7), 2006, 2180-2181.

Fernandez-Rodriguez, et al., "Highly efficient and functional-group-tolerant catalysts for the palladium-catalyzed coupling of aryl chlorides with thiols", Chem.—Eur. J., 12, 2006, 7782-7796.

Gendre, et al., "Solid-phase synthesis of diaryl sulfides: direct coupling of solid-supported aryl halides with thiols using an insoluble polymer-supported reagent", Org. Lett. , 7(13), 2005, 2719-2722.

Gogoi, et al., "Nickel-Schiff base complex catalyzed C—S cross-coupling of thiols with organic chlorides", Tetrahedron, 70, 2014, 7484-7489.

Gorczynski, et al., "Synthesis and evaluation of substituted 4-aryloxy- and 4-arylsulfanyl-phenyl-2-aminothiazoles as inhibitors of human breast cancer cell proliferation", Bioorg. Med. Chem., 12, 2004, 1029-1036.

Grushin, et al., "Transformations of Chloroarenes, Catalyzed by Transition-Metal Complexes", Chem. Rev., 94, 1994, 1047-1062.

Guan, et al., "Efficient nickel/N-heterocyclic carbene catalyzed C—S cross-coupling", Tetrahedron Letters, 53, 2012, 5987-5992.

Hartwig, J. F., "Evolution of a fourth generation catalyst for the amination and thioetherification of aryl halides", Acc. Chem. Res., 41(11), 2008, 1534-1544.

Huang, et al., "Cu-Catalyzed carbon-heteroatom coupling reactions under mild conditions promoted by resin-bound organic ionic bases", J. Org. Chem., 4;76(3), 2011, 800-810.

Ilardi, et al., "Data-mining for sulfur and fluorine: an evaluation of pharmaceuticals to reveal opportunities for drug design and discovery", J. Med. Chem., 57(7), 2014, 2832-2842.

Ischay, et al., "Efficient visible light photocatalysis of [2+2] Enone cycloadditions", J. Am. Chem. Soc., 130(39), 2008, 12886-12887.

Jiang, et al., "Room-Temperature Arylation of Thiols: Breakthrough with Aryl Chlorides", Angew. Chem., Int. Ed., 56(3), 2017, 874-879.

Johnson, et al., "A mechanistic investigation of the photoinduced, copper-mediated cross-coupling of an aryl thiol with an aryl halide", J. C. Chem. Sci., 7(7), 2016, 4091-4100.

Kovacs, et al., "Oxidoreductive coupling of thiols with aryl halides catalyzed by copper on iron", Org. Biomol. Chem., 9, 2011, 711-716.

Kwong, et al., "A general, efficient, and inexpensive catalyst system for the coupling of aryl iodides and thiols", Org. Lett., 4(20), 2002, 3517-3520.

Lima, et al., "Organic Synthesis Enabled by Light-Irradiation of EDA Complexes: Theoretical Background and Synthetic Applications", ACS Catal., 6, 2016, 1389-1407.

Lin, et al., "Odorless, Regioselective Synthesis of Diaryl Sulfides and a-Thioaryl Carbonyls from Sodium Arylsulfinates via a Metal-Free Radical Strategy in Water", Adv. Synth. Catal., 358, 2016, 4100-4105.

(56) References Cited

OTHER PUBLICATIONS

Murata, et al., "A general and efficient method for the palladium-catalyzed cross-coupling of thiols and secondary phosphines", Tetrahedron, 60, 2004, 7397-7403.

Narayanam, et al., "Electron-transfer photoredox catalysis: development of a tin-free reductive dehalogenation reaction", J. Am. Chem. Soc., 131(25), 2009, 8756-8757.

Nicewicz, et al., "Merging photoredox catalysis with organocatalysis: the direct asymmetric alkylation of aldehydes", Science, 322(5898), 2008, 77-80.

Oderinde, et al., "Photoredox Mediated Nickel Catalyzed Cross-Coupling of Thiols With Aryl and Heteroaryl Iodides via Thiyl Radicals", J. Am. Chem. Soc., 138, 2016, 1760-1763.

Patani, et al., "Bioisosterism: A Rational Approach in Drug Design", Chem. Rev., vol. 96, 1996, pp. 3147-3176.

Pawliczek, et al., "Activation of aryl thiocyanates followed by aryne insertion: access to 1,2-thiobenzonitriles", Org. Lett., 17, 2015, 1716-1719.

Pearson, et al., "Organocatalyzed Atom Transfer Radical Polymerization Using N-Aryl Phenoxazines as Photoredox Catalysts", J. Am. Chem. Soc., 138(35), 2016, 11399-11407.

Prasad, et al., "An efficient intermolecular C(aryl)-S bond forming reaction catalyzed by BINAM-copper(II) complex", Tetrahedron Letters, 50, 2009, 1411-1415.

Qiao, et al., "Ligand-Controlled Divergent Cross-Coupling Involving Organosilicon Compounds for Thioether and Thioester Synthesis", Org. Lett., 18, 2016, 1550-1553.

Rahate, et al., "Polyphenylene sulfide (PPS): state of the art and applications", Rev Chem Eng; 29(6), 2013, 471-489.

Rosokha, et al., "Fresh look at electron-transfer mechanisms via the donor/acceptor bindings in the critical encounter complex", Chem. Res., 41(5), 2008, 641-653.

Rossi, et al., "Nucleophilic substitution reactions by electron transfer", Chem. Rev., 103(1), 2003, 71-168.

Savarin, et al., "A mild, nonbasic synthesis of thioethers. The copper-catalyzed coupling of boronic acids with N-thio(alkyl, aryl, heteroaryl)imides", Org. Lett., 4, 2002, 4309-4312.

Sayah, et al., "Carbon-sulfur bond formation of challenging substrates at low temperature by using Pd-PEPPSI-IPent", Chem. Eur. J., 17, 2011, 11719-11722.

Singh, et al., "Convenient MW-assisted synthesis of unsymmetrical sulfides using sulfonyl hydrazides as aryl thiol surrogate", Org. Lett., 15(22), 2013, 5874-5877.

Sun, et al., "Halogen-Bond-Promoted Double Radical Isocyanide Insertion under Visible-Light Irradiation: Synthesis of 2-Fluoroalkylated Quinoxalines", Org. Lett., 18(18), 2016, 4638-4641.

Theriot, et al., "Organocatalyzed atom transfer radical polymerization driven by visible light", Science, 352(6289), 2016, 1082-1086.

Thomas, et al., "A general and inexpensive protocol for the Cu-catalyzed C—S cross-coupling reaction between aryl halides and thiols", Tetrahedron Lett., 56, 2015, 6560-6564.

Uyeda, et al., "A new family of nucleophiles for photoinduced, copper-catalyzed cross-couplings via single-electron transfer: reactions of thiols with aryl halides under mild conditions (O ° C.)", J. Am. Chem. Soc., 135(25), 2013, 9548-9552.

Verma, et al., "A general and efficient CuI/BtH catalyzed coupling of aryl halides with thiols", Tetrahedron Letters, 48, 2007, 7199-7202.

Wang, et al., "A mild, one-pot Stadler-Ziegler synthesis of arylsulfides facilitated by photoredox catalysis in batch and continuous-flow", Angew. Chem., Int. Ed., 52(30), 2013, 7860-7864.

Wang, et al., "Copper-Catalyzed Sulfenylation of Boronic Acids with Sulfonyl Hydrazides", Adv. Synth. Catal., 357, 2015, 928-932.

Wong, et al., "Cobalt-Catalyzed Aryl-Sulfur Bond Formation", Org. Lett., 8, 2006, 5613-5616.

Wu, et al., "Simple N-Heterocyclic Carbenes as Ligands in Ullmann-Type Ether and Thioether Formations", Adv. Synth. Catal., 358, 2016, 1924-1928.

Yan, et al., "The synthesis and SAR of novel diarylsulfone 11β-HSD1 inhibitors", Bioorg. Med. Chem. Lett., 20(23), 2010, 7071-7075.

Yoshida, et al., "A mild and facile synthesis of aryl and alkenyl sulfides via copper-catalyzed deborylthiolation of organoborons with thiosulfonates", Chem. Commun., 51, 2015, 16613-16616.

Zhang, et al., "Facile aromatic nucleophilic substitution (SNAr) reactions in ionic liquids: an electrophile-nucleophile dual activation by [Omim]Br for the reaction", Green Chem., 18, 2016, 5580-5585.

\* cited by examiner $\lambda_{calc,1} = 282\text{nm}$ (f=0.137)
35% ($\pi_{HOMO}\text{-}\pi_{LUMO+4}$)
32% ($\pi_{HOMO}\text{-}\pi_{LUMO+5}$)

$\lambda_{calc,2} = 383\text{nm}$ (f=0.036)
98% ($\pi_{HOMO}\text{-}\pi_{LUMO}$)

FIG. 4A
FIG. 4B
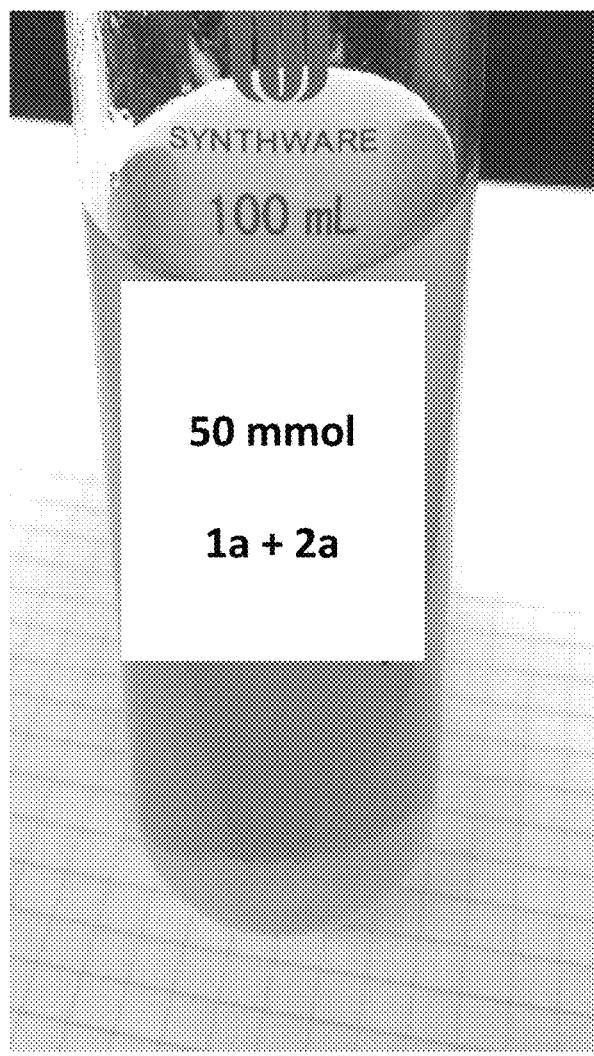
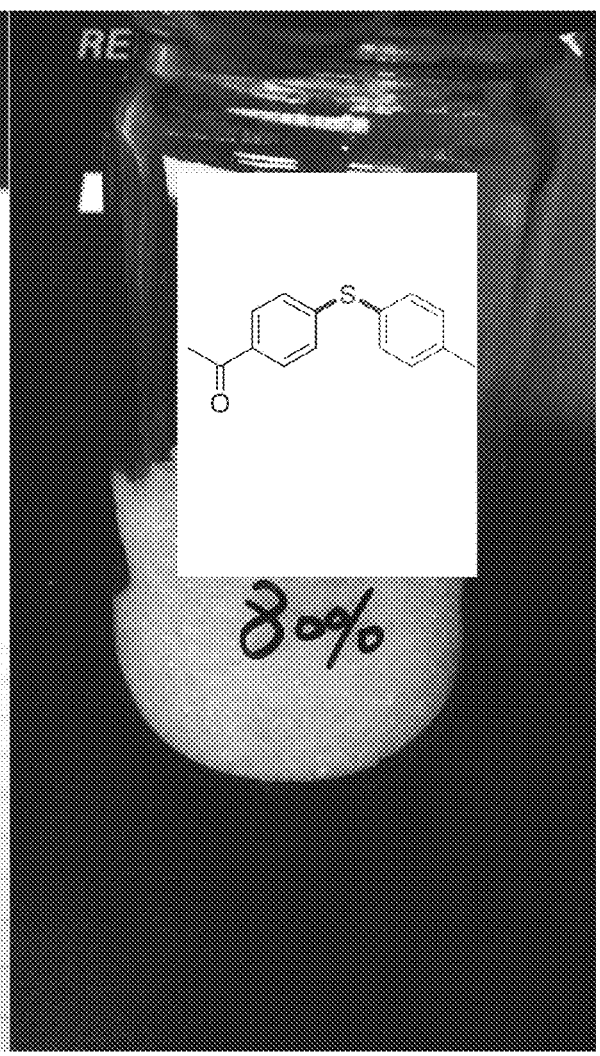

PHOTOCATALYST-FREE, LIGHT-INDUCED CARBON-SULFUR CROSS-COUPLING METHODS

CROSS-REFERENCE TO RELATED APPLICATIONS

The present application claims priority under 35 U.S.C. § 119(e) to U.S. Provisional Application No. 62/525,402, filed Jun. 27, 2017 which is incorporated herein by reference in its entirety.

STATEMENT REGARDING FEDERALLY SPONSORED RESEARCH OR DEVELOPMENT

This invention was made with government support under grant number DE-AR0000683 awarded by the U.S. Department of Energy. The government has certain rights in the invention.

BACKGROUND OF THE INVENTION

Aromatic thioethers are prevalent in a wide range of bioactive natural products and pharmaceuticals, including thymitaq, axitinib, and nelfinavir. Aromatic thioethers are also valuable architectures in drug development, organic materials, and polymers. Thus, the development of environmentally friendly and atom economical methods for constructing C—S bonds are of significant importance with broad impact across pharmaceutical and materials sciences.

Traditionally, transition-metal catalysts are employed to catalyze cross-coupling reactions of thiols with aryl halides, providing a useful approach for C—S bond construction. However, most of the reported methods require strong bases (such as alkoxides, for example t-BuONa and t-BuOK), specific or air sensitive ligands, and high temperature. Such concerns motivate efforts to develop alternative approaches for C—S bonds formation.

Recently, photoredox catalysis has become a powerful strategy for the development of a wide range of reactions under mild conditions, including C—S bond formations. A number of precious and first row transition metal catalyzed photoredox reactions have been reported in the literature in recent years. Nevertheless, need for ruthenium and iridium photoredox catalysts introduce limitations in terms of scalability and sustainability of these processes. In addition, ultraviolet (UV) photo-induced coupling of thiophenoxide with aryl iodides in liquid ammonia was also reported. However, this process requires the use of high energy UV irradiation and can lead to side reactions.

There remains a need in the art for novel methods of making aromatic thioethers in good yields under mild conditions. In certain embodiments, such methods should not require use of expensive reactants and catalysts. In other embodiments, such methods should allow for wide functional group tolerance in producing aryl thioethers. The present invention fulfills these needs.

BRIEF SUMMARY OF THE INVENTION

In one aspect, the invention provides a method of generating a(n) (hetero)aryl thioether.

In certain embodiments, the method comprises irradiating a system comprising a(n) (hetero)aryl halide, a thiol, and at least one base with at least one light wavelength, whereby a carbon-sulfur bond is formed between the (hetero)aryl halide and the thiol.

In certain embodiments, the system is essentially free of at least one catalyst selected from the group consisting of a transition metal and an organic photocatalyst.

In certain embodiments, the system is essentially free of a transition metal and an organic photocatalyst. In other embodiments, the system is free of the at least one catalyst. In yet other embodiments, the system is free of a transition metal and an organic photocatalyst. In yet other embodiments, if the at least one catalyst is present in the system, the at least one catalyst is present at levels that do not promote significant carbon-sulfur bond formation between the (hetero)aryl halide and the thiol.

In certain embodiments, the at least one base is selected from the group consisting of an amine, a phosphine, a carbonate salt, a hydroxide salt, an alkoxide salt, a phosphate salt, a metal hydride and a carboxylate salt. In other embodiments, the at least one base is selected from the group consisting of $Na_2CO_3$, $K_2CO_3$, $Rb_2CO_3$ and $Cs_2CO_3$.

In certain embodiments, the (hetero)aryl halide and the thiol are irradiated with a radiation selected from the group consisting of UV light radiation (about 10 nm to about 380 nm), visible light radiation (about 380 nm to about 700 nm), and natural sunlight radiation. In other embodiments, the (hetero)aryl halide and the thiol are irradiated by a light emitting diode (LED).

In certain embodiments, the (hetero)aryl halide is at least one selected from the group consisting of fluoride chloride, bromide, and iodide.

In certain embodiments, the (hetero)aryl halide is a heteroaryl halide.

In certain embodiments, the (hetero)aryl halide is optionally substituted with at least one additional substituent selected from the group consisting of $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_8$ cycloalkyl, heterocycloalkyl, $C_1$-$C_6$ alkoxy, aryl, heteroaryl, benzyl, heterocyclyl, cyano, halogen, hydroxy, nitro, $S(C_1$-$C_6$ alkyl), —S(=O)($C_1$-$C_6$ alkyl), —S(=O)$_2$($C_1$-$C_6$ alkyl), —S(=O)$_2$ $NH_2$, —S(=O)$_2$NH($C_1$-$C_6$ alkyl), —S(=O)$_2$N ($C_1$-$C_6$ alkyl)($C_1$-$C_6$ alkyl), —NHNH$_2$, —NH$_2$, —NH($C_1$-$C_6$ alkyl optionally substituted with 1-2 OH), —N($C_1$-$C_6$ alkyl optionally substituted with 1-2 OH)($C_1$-$C_6$ alkyl optionally substituted with 1-2 OH), —NHC(=O)($C_1$-$C_6$ alkyl), —N($C_1$-$C_6$ alkyl)C(=O)O($C_1$-$C_6$ alkyl), —(CH$_2$)$_n$ CHO, —(CH$_2$)$_n$C(=O)OH, —(CH$_2$)$_n$C(=O)O($C_1$-$C_6$ alkyl), —C(=O)S($C_1$-$C_6$ alkyl), —(CH$_2$)$_n$C(=O)NH$_2$, —(CH$_2$)$_n$C(=O)NH($C_1$-$C_6$ alkyl), —(CH$_2$)$_n$C(=O)N($C_1$-$C_6$ alkyl)($C_1$-$C_6$ alkyl), —(CH$_2$)$_n$C(=O)($C_1$-$C_6$ alkyl), —(CH$_2$)$_n$C(=O)(aryl), —(CH$_2$)$_n$C(=O)(heteroaryl), —(CH$_2$)$_n$C(=O)(heterocyclyl), —(CH$_2$)$_n$OC(=O)O($C_1$-$C_6$ alkyl), —OC(=O)NH$_2$, —OC(=O)NH($C_1$-$C_6$ alkyl), —OC(=O)N($C_1$-$C_6$ alkyl)($C_1$-$C_6$ alkyl), —(CH$_2$)$_n$NHC (=O)($C_1$-$C_6$ alkyl), —(CH$_2$)$_n$N($C_1$-$C_6$ alkyl)C(=O)($C_1$-$C_6$ alkyl), wherein each occurrence of n is independently an integer selected from the group consisting of 0, 1, 2, 3, 4, 5, and 6, and wherein two adjacent substituents on the (hetero) aryl are taken together to form $C_1$-$C_6$ cycloalkylene, $C_1$-$C_6$ heterocycloalkylene, fused aryl, or fused heteroaryl; wherein each moiety selected from the group consisting of alkyl, —CH$_2$—, alkenyl, alkynyl, heteroalkyl, heteroalkenyl, heteroalkynyl, cycloalkyl, heterocycloalkyl, aryl, heteroaryl, heterocyclyl, benzyl, cycloalkylene, and heterocycloalkylene is independently optionally substituted with at least one selected from the group consisting of $C_1$-$C_6$ alkyl, $C_1$-$C_6$ alkoxy, aryl, heteroaryl, heterocyclyl, OH, halogen, —NH$_2$, —NH($C_1$-$C_6$ alkyl optionally substituted with 1-2 OH), —N($C_1$-$C_6$ alkyl optionally substituted with 1-2 OH)

($C_1$-$C_6$ alkyl optionally substituted with 1-2 OH), —C(=O)OH, and —C(=O)($C_1$-$C_6$ alkyl); or wherein two moieties on the same N atom of the at least additional substituent, or moieties on two different atoms of the at least additional substituent, combine to form $C_3$-$C_8$ heterocyclyl.

In certain embodiments, the thiol is selected from the group consisting of optionally substituted $C_1$-$C_6$ alkylthiol, thiophenol, thionaphthol, thioanthracenol, thiophenanthrol, thiopyrenol, benzyl mercaptan, heteroaryl thiol, and heteroarylmethyl thiol.

In certain embodiments, the thiol is optionally substituted with at least one additional substituent selected from the group consisting of $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_8$ cycloalkyl, heterocycloalkyl, $C_1$-$C_6$ alkoxy, aryl, heteroaryl, benzyl, heterocyclyl, cyano, halogen, hydroxy, nitro, S($C_1$-$C_6$ alkyl), —S(=O)($C_1$-$C_6$ alkyl), —S(=O)$_2$($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)($C_1$-$C_6$ alkyl), —NHNH$_2$, —NH$_2$, —NH($C_1$-$C_6$ alkyl optionally substituted with 1-2 OH), —N($C_1$-$C_6$ alkyl optionally substituted with 1-2 OH)($C_1$-$C_6$ alkyl optionally substituted with 1-2 OH), —NHC(=O)O($C_1$-$C_6$ alkyl), —N($C_1$-$C_6$ alkyl)C(=O)O($C_1$-$C_6$ alkyl), —(CH$_2$)$_n$CHO, —(CH$_2$)$_n$C(=O)OH, —(CH$_2$)$_n$C(=O)O($C_1$-$C_6$ alkyl), —C(=O)S($C_1$-$C_6$ alkyl), —(CH$_2$)$_n$C(=O)NH$_2$, —(CH$_2$)C(=O)NH($C_1$-$C_6$ alkyl), —(CH$_2$)$_n$C(=O)N($C_1$-$C_6$ alkyl)($C_1$-$C_6$ alkyl), —(CH$_2$)$_n$C(=O)($C_1$-$C_6$ alkyl), —(CH$_2$)$_n$C(=O)(aryl), —(CH$_2$)$_n$C(=O)(heteroaryl), —(CH$_2$)$_n$C(=O)(heterocyclyl), —(CH$_2$)$_n$OC(=O)O($C_1$-$C_6$ alkyl), —OC(=O)NH$_2$, —OC(=O)NH($C_1$-$C_6$ alkyl), —OC(=O)N($C_1$-$C_6$ alkyl)($C_1$-$C_6$ alkyl), —(CH$_2$)$_n$NHC(=O)($C_1$-$C_6$ alkyl), —(CH$_2$)$_n$N($C_1$-$C_6$ alkyl)C(=O)($C_1$-$C_6$ alkyl), wherein each occurrence of n is independently an integer selected from the group consisting of 0, 1, 2, 3, 4, 5, and 6, and wherein two adjacent substituents on the thiol are taken together to form $C_1$-$C_6$ cycloalkylene, $C_1$-$C_6$ heterocycloalkylene, fused aryl, or fused heteroaryl; wherein each moiety selected from the group consisting of alkyl, —CH$_2$—, alkenyl, alkynyl, heteroalkyl, heteroalkenyl, heteroalkynyl, cycloalkyl, heterocycloalkyl, aryl, heteroaryl, heterocyclyl, benzyl, cycloalkylene, and heterocycloalkylene is independently optionally substituted with at least one selected from the group consisting of $C_1$-$C_6$ alkyl, $C_1$-$C_6$ alkoxy, aryl, heteroaryl, heterocyclyl, OH, halogen, —NH$_2$, —NH($C_1$-$C_6$ alkyl optionally substituted with 1-2 OH), —N($C_1$-$C_6$ alkyl optionally substituted with 1-2 OH)($C_1$-$C_6$ alkyl optionally substituted with 1-2 OH), —C(=O)OH, and —C(=O)($C_1$-$C_6$ alkyl); or wherein two moieties on the same N atom of the at least additional substituent, or moieties on two different atoms of the at least additional substituent, combine to form $C_3$-$C_8$ heterocyclyl.

In certain embodiments, the (hetero)aryl thioether comprises a first monovalent moiety and a second divalent moiety coupled to a —S— divalent group, wherein the first monovalent moiety is selected from the group consisting of phenyl and heteroaryl, and wherein the second monovalent moiety is selected from the group consisting of phenyl, benzyl, heteroaryl, and heteroarylmethyl, all of which are optionally independently substituted.

In certain embodiments, the system further comprises at least one solvent. In other embodiments, the at least one solvent is a polar and aprotic organic solvent. In yet other embodiments, the at least one solvent is selected from the group consisting of dimethyl sulfoxide (DMSO), dimethyl formamide (DMF), dimethyl acetamide (DMA) and acetonitrile (CH$_3$CN).

In certain embodiments, the system is under an inert, oxygen-free atmosphere.

In certain embodiments, the (hetero)aryl thioether is a polymer comprising thioether linkages.

BRIEF DESCRIPTION OF THE DRAWINGS

For the purpose of illustrating the invention, certain embodiments of the invention are depicted in the drawings. However, the invention is not limited to the precise arrangements and instrumentalities of the embodiments depicted in the drawings.

FIGS. 4A-4B are a pair of photographs of a multi-gram scale C—S coupling experiment of the invention. FIG. 4A is a photograph of the reaction mixture after irradiation. FIG. 4B is a photograph of the isolated C—S coupled product

DETAILED DESCRIPTION OF THE INVENTION

Figure 1:
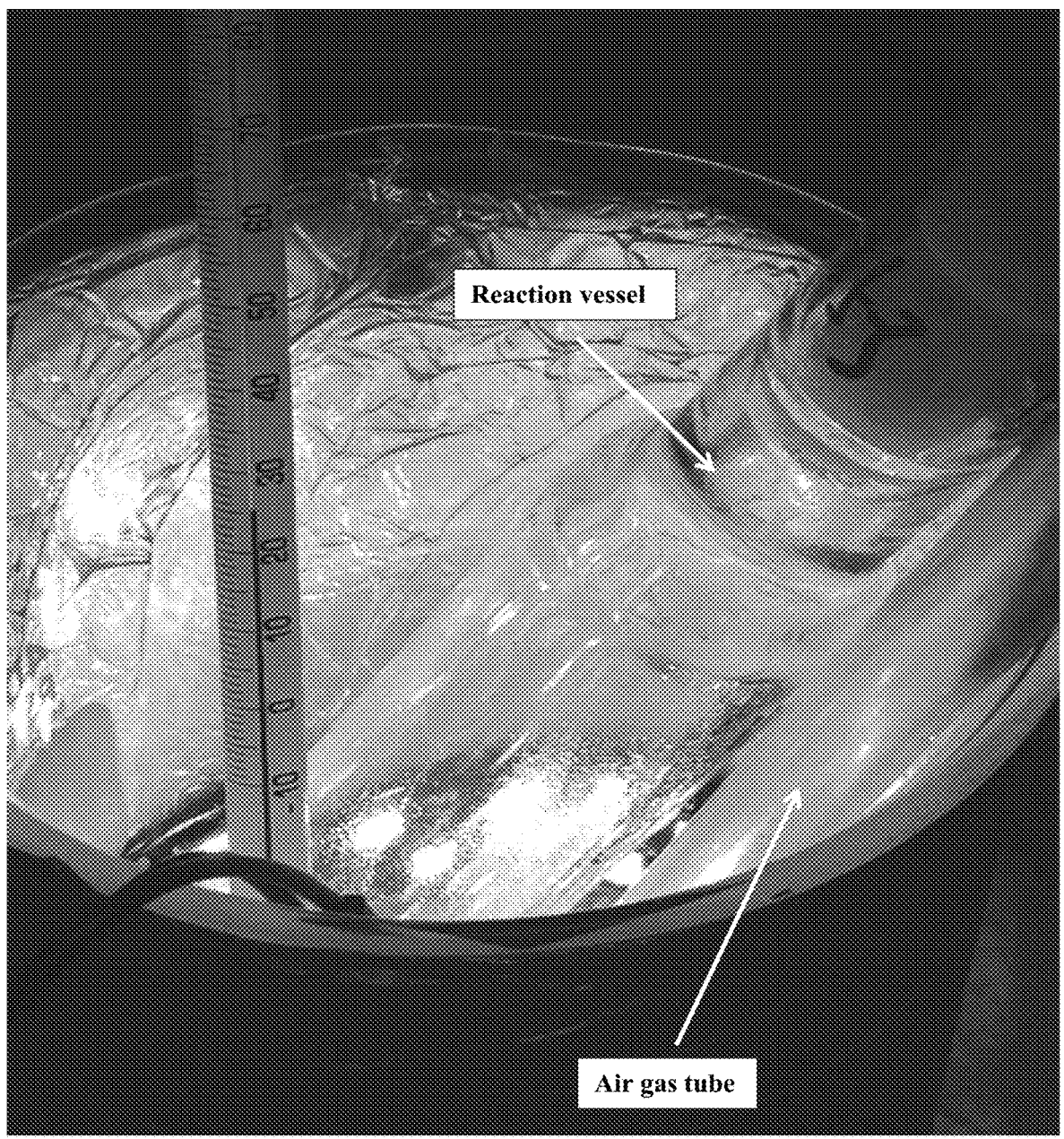
FIG. 1 is a photograph of the reaction setup for C—S bond formation reactions using visible light LED beakers, according to a non-limiting embodiment of the invention.

The invention relates to the unexpected discovery that light-promoted carbon-sulfur bond forming reactions can be carried out in the absence of any transition metal or organic photocatalyst, and under mild conditions. In one aspect, the invention provides a method of promoting a carbon-sulfur bond forming reaction. In certain embodiments, the method promotes the cross-coupling reaction of a(n) (hetero)aryl halide with a thiol to form a carbon-sulfur bond, wherein the reaction is promoted by light irradiation in the absence of a photocatalyst. In other embodiments, the cross-coupling reaction is promoted through visible light irradiation, including ambient sunlight. In yet other embodiments, the cross-coupling reaction is tolerant of various electronically and sterically hindering substituents on the (hetero)aryl halide and thiol substrates. In yet other embodiments, the cross-coupling reaction can utilize mild and inexpensive bases, such as K$_2$CO$_3$ and Cs$_2$CO$_3$, to help drive the reaction.

Methods

The invention provides a method of generating a(n) (hetero)aryl thioether, the method comprising irradiating with at least one light wavelength a system comprising a(n) (hetero)aryl halide, a thiol, and at least one base, whereby the (hetero)aryl halide and the thiol react to form a carbon-sulfur bond.

In certain embodiments, the (hetero)aryl halide is at least one selected from the group consisting of an (hetero)aryl fluoride, (hetero)aryl chloride, (hetero)aryl bromide, and (hetero)aryl iodide. In yet other embodiments, the (hetero)

aryl halide is an optionally substituted aryl halide, such as but not limited to phenyl halide, naphthyl halide, anthracenyl halide, phenanthryl halide, or pyrenyl halide. In yet other embodiments, the (hetero)aryl halide is an optionally substituted heteroaryl halide. In yet other embodiments, the (hetero)aryl halide is an optionally substituted heteroaryl halide, such as but not limited to a pyrimidyl halide, pyridyl halide, and/or quinolyl halide. In yet other embodiments, the (hetero)aryl halide is optionally substituted with at least one additional substituent selected from the group consisting of $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_8$ cycloalkyl, heterocycloalkyl, $C_1$-$C_6$ alkoxy, aryl (such as phenyl or naphthyl), heteroaryl, benzyl, heterocyclyl, cyano, halogen, hydroxy, nitro, S($C_1$-$C_6$ alkyl), —S(=O)($C_1$-$C_6$ alkyl), —S(=O)$_2$($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)($C_1$-$C_6$ alkyl), —NHNH$_2$, —NH$_2$, —NH($C_1$-$C_6$ alkyl optionally substituted with 1-2 OH), —N($C_1$-$C_6$ alkyl optionally substituted with 1-2 OH)($C_1$-$C_6$ alkyl optionally substituted with 1-2 OH), —NHC(=O)O($C_1$-$C_6$ alkyl), —N($C_1$-$C_6$ alkyl)C(=O)O($C_1$-$C_6$ alkyl), —(CH$_2$)$_n$CHO, —(CH$_2$)$_n$C(=O)OH, —(CH$_2$)$_n$C(=O)O($C_1$-$C_6$ alkyl), —C(=O)S($C_1$-$C_6$ alkyl), —(CH$_2$)$_n$C(=O)NH$_2$, —(CH$_2$)$_n$C(=O)NH($C_1$-$C_6$ alkyl), —(CH$_2$)$_n$C(=O)N($C_1$-$C_6$ alkyl)($C_1$-$C_6$ alkyl), —(CH$_2$)$_n$C(=O)($C_1$-$C_6$ alkyl), —(CH$_2$)$_n$C(=O)(aryl), —(CH$_2$)$_n$C(=O)(heteroaryl), —(CH$_2$)$_n$C(=O)(heterocyclyl), —(CH$_2$)$_n$OC(=O)O($C_1$-$C_6$ alkyl), —OC(=O)NH$_2$, —OC(=O)NH($C_1$-$C_6$ alkyl), —OC(=O)N($C_1$-$C_6$ alkyl)($C_1$-$C_6$ alkyl), —(CH$_2$)$_n$NHC(=O)($C_1$-$C_6$ alkyl), —(CH$_2$)$_n$N($C_1$-$C_6$ alkyl)C(=O)($C_1$-$C_6$ alkyl), wherein each occurrence of n is independently an integer ranging from 0-6, and wherein two adjacent substituents on the (hetero)aryl are taken together to form $C_1$-$C_6$ cycloalkylene, $C_1$-$C_6$ heterocycloalkylene, fused aryl, or fused heteroaryl;

wherein each moiety selected from the group consisting of alkyl, —CH$_2$—, alkenyl, alkynyl, heteroalkyl, heteroalkenyl, heteroalkynyl, cycloalkyl, heterocycloalkyl, aryl, heteroaryl, heterocyclyl, benzyl, cycloalkylene, and heterocycloalkylene is independently optionally substituted with at least one selected from the group consisting of $C_1$-$C_6$ alkyl, $C_1$-$C_6$ alkoxy, aryl, heteroaryl, heterocyclyl, OH, halogen, —NH$_2$, —NH($C_1$-$C_6$ alkyl optionally substituted with 1-2 OH), —N($C_1$-$C_6$ alkyl optionally substituted with 1-2 OH)($C_1$-$C_6$ alkyl optionally substituted with 1-2 OH), —C(=O)OH, and —C(=O)($C_1$-$C_6$ alkyl); or wherein two moieties on the same N atom of the at least additional substituent, or moieties on two different atoms of the at least additional substituent, combine to form $C_3$-$C_8$ heterocyclyl.

In certain embodiments, the thiol is an optionally substituted aryl thiol or benzylic thiol. In other embodiments, the thiol is an optionally substituted thiophenol, thionaphthol, thioanthracenol, thiophenanthrol, thiopyrenol, or benzyl mercaptan. In yet other embodiments, the thiol is an optionally substituted heteroaryl thiol or heteroarylmethyl thiol, such as but not limited to a mercaptopyridine, mercaptopyrimidine, 2-mercaptobenzimidazole, 2-mercaptobenzothiazole, or 7-mercapto-4-methylcoumarin. In yet other embodiments, the thiol is an optionally substituted $C_1$-$C_6$ alkylthiol. In yet other embodiments, the thiol is optionally substituted with at least one additional substituent selected from the group consisting of $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_8$ cycloalkyl, heterocycloalkyl, $C_1$-$C_6$ alkoxy, aryl (such as phenyl or naphthyl), heteroaryl, benzyl, heterocyclyl, cyano, halogen, hydroxy, nitro, S($C_1$-$C_6$ alkyl), —S(=O)($C_1$-$C_6$ alkyl), —S(=O)$_2$($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)($C_1$-$C_6$ alkyl), —NHNH$_2$, —NH$_2$, —NH($C_1$-$C_6$ alkyl optionally substituted with 1-2 OH), —N($C_1$-$C_6$ alkyl optionally substituted with 1-2 OH)($C_1$-$C_6$ alkyl optionally substituted with 1-2 OH), —NHC(=O)O($C_1$-$C_6$ alkyl), —N($C_1$-$C_6$ alkyl)C(=O)O($C_1$-$C_6$ alkyl), —(CH$_2$)$_n$CHO, —(CH$_2$)$_n$C(=O)OH, —(CH$_2$)$_n$C(=O)O($C_1$-$C_6$ alkyl), —C(=O)S($C_1$-$C_6$ alkyl), —(CH$_2$)$_n$C(=O)NH$_2$, —(CH$_2$)$_n$C(=O)NH($C_1$-$C_6$ alkyl), —(CH$_2$)$_n$C(=O)N($C_1$-$C_6$ alkyl)($C_1$-$C_6$ alkyl), —(CH$_2$)$_n$C(=O)($C_1$-$C_6$ alkyl), —(CH$_2$)$_n$C(=O)(aryl), —(CH$_2$)$_n$C(=O)(heteroaryl), —(CH$_2$)$_n$C(=O)(heterocyclyl), —(CH$_2$)$_n$OC(=O)O($C_1$-$C_6$ alkyl), —OC(=O)NH$_2$, —OC(=O)NH($C_1$-$C_6$ alkyl), —OC(=O)N($C_1$-$C_6$ alkyl)($C_1$-$C_6$ alkyl), —(CH$_2$)$_n$NHC(=O)($C_1$-$C_6$ alkyl), —(CH$_2$)$_n$N($C_1$-$C_6$ alkyl)C(=O)($C_1$-$C_6$ alkyl), wherein each occurrence of n is independently an integer ranging from 0-6, and wherein two adjacent substituents on the thiol are taken together to form $C_1$-$C_6$ cycloalkylene, $C_1$-$C_6$ heterocycloalkylene, fused aryl, or fused heteroaryl;

wherein each moiety selected from the group consisting of alkyl, —CH$_2$—, alkenyl, alkynyl, heteroalkyl, heteroalkenyl, heteroalkynyl, cycloalkyl, heterocycloalkyl, aryl, heteroaryl, heterocyclyl, benzyl, cycloalkylene, and heterocycloalkylene is independently optionally substituted with at least one selected from the group consisting of $C_1$-$C_6$ alkyl, $C_1$-$C_6$ alkoxy, aryl, heteroaryl, heterocyclyl, OH, halogen, —NH$_2$, —NH($C_1$-$C_6$ alkyl optionally substituted with 1-2 OH), —N($C_1$-$C_6$ alkyl optionally substituted with 1-2 OH)($C_1$-$C_6$ alkyl optionally substituted with 1-2 OH), —C(=O)OH, and —C(=O)($C_1$-$C_6$ alkyl); or wherein two moieties on the same N atom of the at least additional substituent, or moieties on two different atoms of the at least additional substituent, combine to form $C_3$-$C_8$ heterocyclyl.

In certain embodiments, the thioether product is any thioether that can be made by the cross-coupling of any (hetero)aryl halide described elsewhere herein with any thiol described elsewhere herein. In other embodiments, the thioether product is any thioether disclosed elsewhere herein. In yet other embodiments, the thioether product comprises a first monovalent moiety and a second divalent moiety that are coupled to a —S— divalent group, wherein the first monovalent moiety is selected from the group consisting of phenyl and heteroaryl, and wherein the second monovalent moiety is selected from the group consisting of phenyl, benzyl, heteroaryl, and heteroarylmethyl, all of which are independently optionally substituted.

In certain embodiments, the at least one base is a carbonate salt. In other embodiments, the at least one base is selected from the group consisting of Na$_2$CO$_3$, K$_2$CO$_3$, Rb$_2$CO$_3$, and Cs$_2$CO$_3$. In yet other embodiments, the at least one base is an organic base. In yet other embodiments, the at least one base is triazabicyclodecene (TBD). In yet other embodiments, the at least one base is selected from the group consisting of a hydroxide, alkoxide, phosphate, carboxylate, metal hydride, amine, and phosphine. In certain embodiments, the at least one base deprotonates at least a portion of the thiol. In other embodiments, the at least one base has a pKb less than about 5, less than about 4, less than about 3, less than about 1, less than about 0 or less than about −2.

In certain embodiments, the (hetero)aryl halide and the thiol are irradiated with at least one selected from UV light radiation (about 10 nm to about 380 nm), visible light radiation (about 380 nm to about 700 nm) and natural sunlight radiation. In certain embodiments, the irradiation is provided by an artificial light source, such as but not limited to, an LED (light emitting diode), a light bulb, or a UV lamp. In other embodiments, the irradiation is provided by a natural light source, such as the sun. In yet other embodiments, the reaction to form the carbon-sulfur bond does not proceed in the absence of irradiation. In yet other embodiments, the UV light radiation has a wavelength of about 200 nm to about 380 nm.

In certain embodiments, the reaction is promoted in the absence of any photocatalytic species. In other embodiments, the method does not comprise the use of any transition metal catalyst. In yet other embodiments, the method is essentially transition metal free. In yet other embodiments, the method does not comprise the use of any organic photocatalysts. In yet other embodiments, the method does not comprise the use of any additional organic reagent or catalyst beyond the alkyl halide and the thiol.

In certain embodiments, the (hetero)aryl halide, thiol, and at least one base are contacted in a solution comprising at least one solvent. In other embodiments, the solution comprises at least one organic solvent. In yet other embodiments, the solution comprises at least one aprotic solvent. In yet other embodiments, the solution comprises at least one polar solvent. In yet other embodiments, the solution comprises at least one solvent selected from the group consisting of dimethyl sulfoxide (DMSO), dimethyl formamide (DMF), dimethyl acetamide (DMA), and acetonitrile ($CH_3CN$).

In certain embodiments, the (hetero)aryl halide and the thiol are contacted under an inert, air-free atmosphere. In other embodiments, the inert atmosphere comprises, but is not necessarily limited to, nitrogen and/or argon.

In certain embodiments, the reaction is conducted at a temperature of about 20° C. to about 100° C. In other embodiments, the reaction is conducted at a temperature of about 20° C. to about 30° C. In yet other embodiments, the reaction is conducted at a temperature of about 30° C. to about 100° C. In yet other embodiments, the reaction is conducted at a temperature of about 25° C. In yet other embodiments, the reaction is maintained at a desired temperature until the reaction is completed. In yet other embodiments, the temperature is regulated through the use of cooling system, such as a compressed gas cooling system.

In certain embodiments, the method of the invention can be used to form polymers having thioether linkages. In other embodiments, the (hetero)aryl halide comprises at least two halide functionalities. In yet other embodiments, the thiol comprises at least two thiol functionalities. In yet other embodiments, the (hetero)aryl halide and the thiol are part of a single compound having both at least one halide functionality and at least one thiol functionality.

Figure 2A:
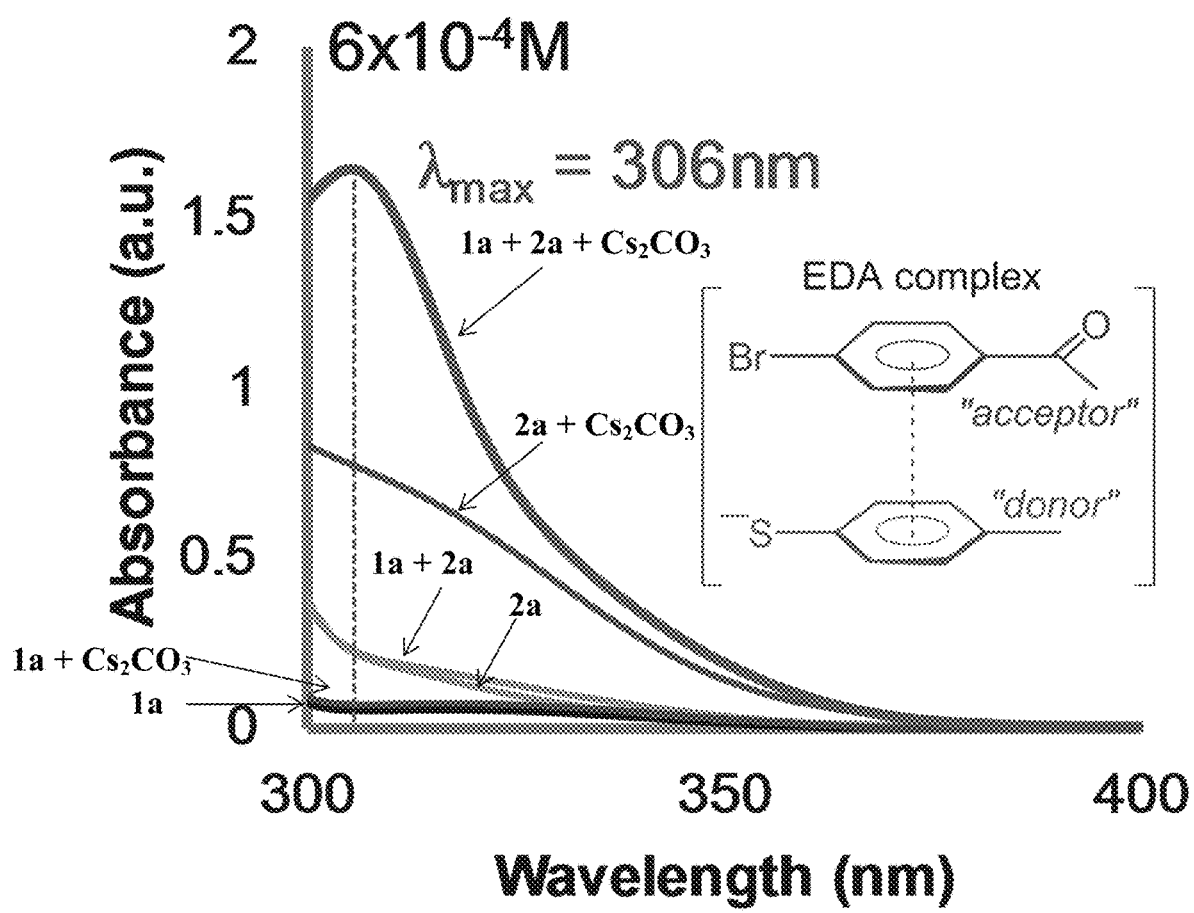
FIGS. 2A-2B show UV-vis absorption spectra of mixtures of 1a, 2a and Cs$_2$CO$_3$ in DMSO measured using a quartz cuvette (path length=1 cm) at concentrations of 6×10$^{-4}$M (FIG. 2A) and 0.1 M for each species (FIG. 2B).
Figure 2B:
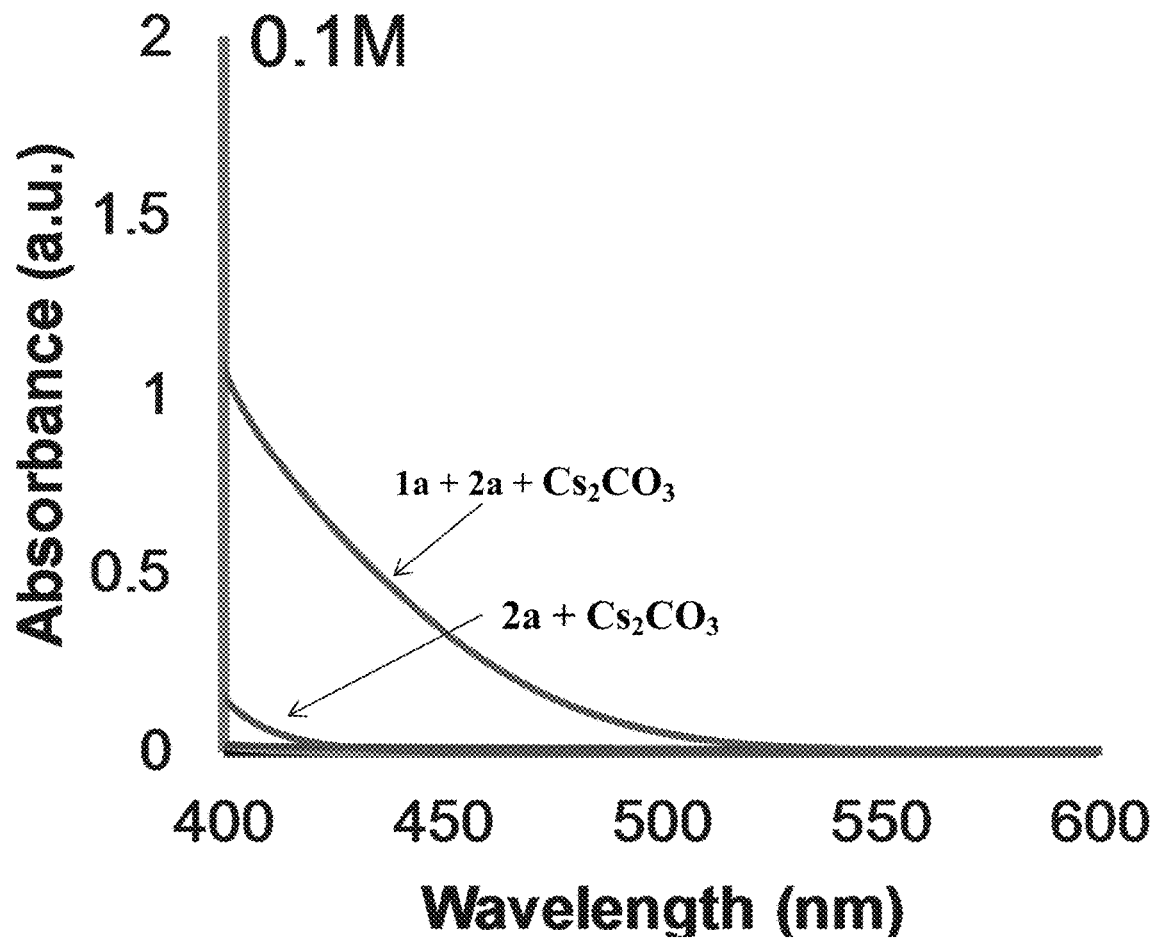
Figure 2C:
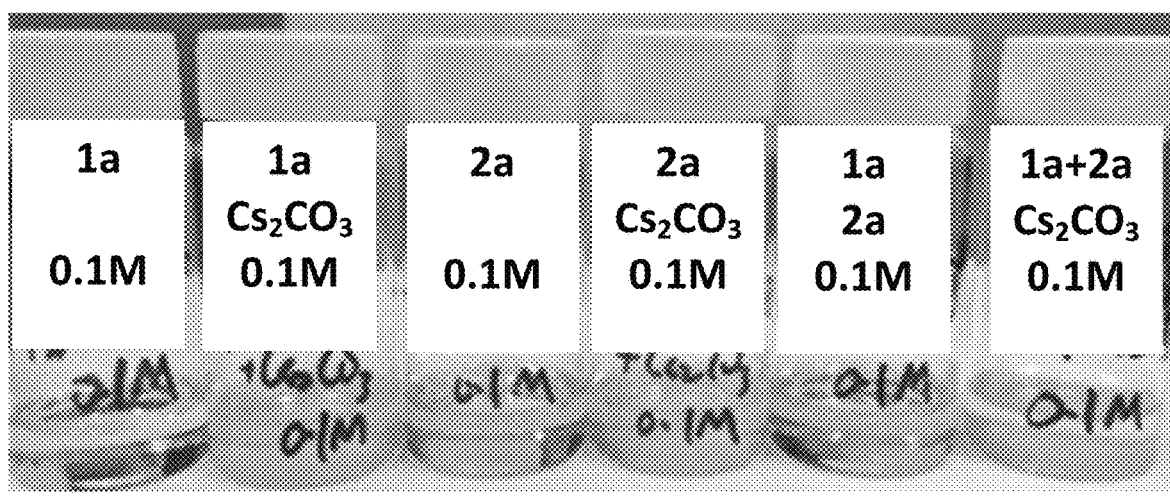
FIG. 2C is a photograph showing the formation of a yellow compound (proposed electron donor-acceptor [EDA] complex) when 1a, 2a, and Cs$_2$CO$_3$ were mixed together while the other mixtures were colorless.
Figure 2D:
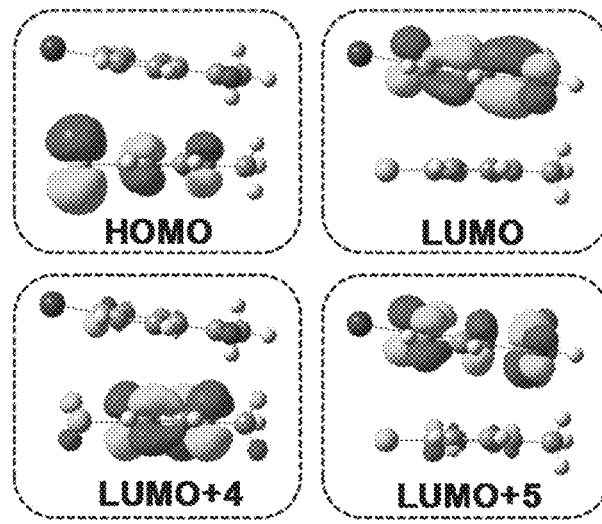
FIG. 2D shows the results of time-dependent DFT calculations to predict UV-vis absorptions of the EDA complex and to assign orbitals involved in the corresponding absorptions.
Figure 2E:
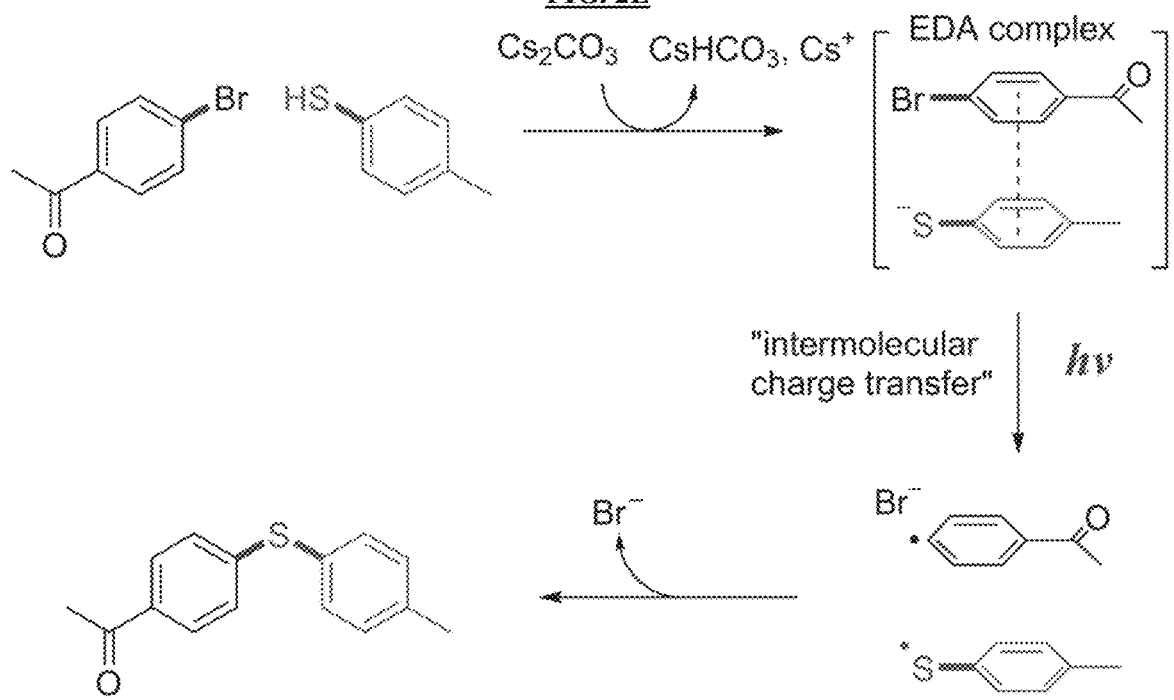
FIG. 2E is a scheme showing a non-limiting, proposed mechanism for visible-light induced C—S cross-coupling.
Figure 3:
FIG. 3 is a picture of the set-up for a sunlight-driven reaction according to an embodiment of the invention.

Without intending to be limited to any particular theory, the method of the invention can proceed through a mechanism as outlined in FIG. 2E, whereby the thiol is deprotonated by the base to form a thiolate, allowing for formation of an electron donor-acceptor (EDA) complex between the thiolate and the (hetero)aryl halide. Irradiation causes an intermolecular charge transfer whereby an electron is transferred from the thiolate to the (hetero)aryl halide, causing dissociation of the halide, and the resulting (hetero)aryl radical and thiolate radical couple to form a C—S bond. In certain embodiments, the at least one base deprotonates at least a portion of the thiol. In other embodiments, the irradiation is of appropriate energy and wavelength to promote intermolecular charge transfer between the thiolate and the (hetero)aryl halide.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in catalysis, photochemistry and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "essentially free" of a catalyst as applied to a method of the invention indicates that the reaction mixture contains less than about 5 mol %, or less than about 1 mol %, or less than about 0.5 mol %, or less than about 0.1 mol %, or less than about 0.05 mol %, or less than about 0.01 mol %, or less than about 0.001 mol %, of any catalytic compound or species as compared to the reaction substrates. In certain embodiments, "essentially free" is taken to mean that the concentration of the catalytic species is low enough so as to not have any significant or measurable effect on the rate of the reaction in question.

As used herein, the term "electromagnetic radiation" includes radiation of one or more frequencies encompassed within the electromagnetic spectrum. Non-limiting examples of electromagnetic radiation comprise gamma radiation, X-ray radiation, UV radiation, visible radiation, infrared radiation, microwave radiation, radio waves, and electron beam (e-beam) radiation. In one aspect, electromagnetic radiation comprises ultraviolet radiation (wavelength from about 10 nm to about 380 nm), visible radiation (wavelength from about 380 nm to about 700 nm) or infrared radiation (radiation wavelength from about 700 nm to about 1 mm). Ultraviolet or UV light as described herein includes UVA light, which generally has wavelengths between about 320 and about 400 nm, UVB light, which generally has wavelengths between about 290 nm and about 320 nm, and UVC light, which generally has wavelengths between about 200 nm and about 290 nm. UV light may include UVA, UVB, or UVC light alone or in combination with other type of UV light. In one embodiment, the UV light source emits light between about 350 nm and about 400 nm. In some embodiments, the UV light source emits light between about 400 nm and about 500 nm. In other embodiments, the reactions of the invention are performed in unfiltered sunlight. In yet other embodiments, the reactions of the invention are performed in at least partially filtered sunlight. In yet other embodiments, the reactions of the invention are performed under a light source that mimics at least a portion of the sunlight spectrum, but yet is more intense than average sunlight radiation.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "reaction condition" refers to a physical treatment, chemical reagent, or combination thereof, which is required or optionally required to promote a reaction. Non-limiting examples of reaction conditions are electromagnetic radiation (such as, but not limited to visible light and UV light), heat, a catalyst, a chemical reagent (such as, but not limited to, an acid, base, electrophile or nucleophile), and a buffer.

As used herein, the term "significant," as applied to a method of the invention, refers to an amount of change that is small enough so that it cannot be reliably measured when compared to a control experiment. For example, methods wherein a catalyst species is present but at levels that do not promote significant carbon-sulfur bond formation indicates that the amount of carbon-sulfur bond formation when the level of catalyst is present is not measurably different from the amount of carbon-sulfur bond formation in the complete absence of the catalyst.

As used herein, the term "alkyl", by itself or as part of another substituent means, unless otherwise stated, a straight or branched chain hydrocarbon having the number of carbon atoms designated (i.e., $C_1$-$C_{15}$ means one to fifteen carbon atoms) and includes straight, branched chain, or cyclic substituent groups. Examples include methyl, ethyl, propyl, isopropyl, butyl, isobutyl, tert-butyl, pentyl, neopentyl, hexyl, cyclopropylmethyl, and dodecanyl. Most preferred is ($C_1$-$C_6$)alkyl, such as, but not limited to, ethyl, methyl, isopropyl, isobutyl, n-pentyl, n-hexyl and cyclopropylmethyl.

As used herein, the term "cycloalkyl", by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl", employed alone or in combination with other terms, means, unless otherwise stated, a stable mono-unsaturated, di-unsaturated, or tri-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—$CH$=$CH_2$.

As used herein, the term "alkynyl", employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers.

As used herein, the term "alkylene" by itself or as part of another substituent means, unless otherwise stated, a straight or branched hydrocarbon group having the number of carbon atoms designated (i.e., $C_1$-$C_{15}$ means one to fifteen carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene. Heteroalkylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group.

As used herein, the term "alkenylene", employed alone or in combination with other terms, means, unless otherwise stated, a stable mono-unsaturated or di-unsaturated straight chain or branched chain hydrocarbon group having the stated number of carbon atoms wherein the group has two open valencies.

As used herein, the term "alkynylene", employed alone or in combination with other terms, means, unless otherwise stated, a stable straight chain or branched chain hydrocarbon group with a triple carbon-carbon bond, having the stated number of carbon atoms wherein the group has two open valencies.

As used herein, the term "substituted alkyl", "substituted cycloalkyl", "substituted alkenyl", "substituted alkynyl", "substituted alkylene", "substituted alkenylene" or "substituted alkynylene" means alkyl, cycloalkyl, alkenyl, alkynyl, alkylene, alkenylene, alkynylene as defined above, substituted by one, two or three substituents selected from the group consisting of $C_1$-$C_{10}$ alkyl, halogen, =O, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl", employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, isoxazolyl, pyrazolyl, isothiazolyl, diazolyl, 1,2,3-triazolyl, 1,2,4-triazolyl, isothiazolyl, 1,3,4-triazolyl, tetrazolyl, 1,2,3-thiadiazolyl, 1,2,3-oxadiazolyl, 1,3,4-thiadiazolyl, and 1,3,4-oxadiazolyl.

Examples of polycyclic heterocycles include isosorbide, isomannide, isoidide, lupeol, indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

Unless otherwise noted, when two substituents are taken together to form a ring having a specified number of ring atoms (e.g., $R^2$ and $R^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following non-limiting abbreviations are used herein: C—S, carbon-sulfur; DFT, density functional theory; DMF, dimethyl formamide; DMSO, dimethyl sulfoxide; EDA, electron donor-acceptor; EtOAc, ethyl acetate; HPLC, high performance liquid chromatography; LED, light emitting diode; NMR, nuclear magnetic resonance spectroscopy; S$_N$Ar, nucleophilic aromatic substitution; TD-DFT, time-dependent density functional theory; TLC, thin layer chromatography; UV, ultraviolet; UV-vis, ultraviolet/visible.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Materials

DMSO was purchased from Sigma-Aldrich and sparged with nitrogen for 15 min at room temperature and stored under nitrogen atmosphere. 4'-Bromoacetophenone and p-Toluenethiol were purchased from TCI America. $Cs_2CO_3$ (REAGENTPLUS®, 99%) was purchased from Sigma-Aldrich. Aryl halides and thiols were purchased from Sigma-Aldrich, TCI or Alfa Aesar. Organic solutions were concentrated under reduced pressure on a Buchi rotary evaporator using a water bath. One, sixteen inch strip of double-density white LEDs, purchased from Creative Lighting Solutions (item no. CL-FRS1210-5M-12V-WH), was wrapped inside a 400 mL beaker and used as a visible light source.

Characterization and Spectroscopy Methods

The emission spectrum of the white LEDs was measured with an Ocean Optics ADC1000 spectrometer.

The $^1H$ and $^{13}C$ NMR spectra were recorded at 300 MHz, 400 MHz or 500 MHz for $^1H$ or at 75 MHz, 100 MHz or 125 MHz for $^{13}C$, respectively. Deuterated solvents were purchased from Cambridge Isotope Laboratories (Andover, Mass.) and used as received. All $^1H$ NMR experiments are reported in δ units, parts per million (ppm), and were measured relative to the signals for residual chloroform (7.26 ppm) in the deuterated solvents. Data for $^1H$ NMR are reported as follows: chemical shift (δ ppm), multiplicity (s=singlet, d=doublet, t=triplet, q=quartet, p=quintet, m=multiplet, dd=doublet of doublets, dt=doublet of triplets . . . etc, br=broad), coupling constant (Hz) and integration. All $^{13}C$ NMR spectra are reported in ppm relative to $CDCl_3$ (77.0 ppm). Trimethyoxybenzene was used as an internal standard for NMR yields from proton analysis for the C—S bond formation reaction.

Flash column chromatography was performed by using a 100-150 times weight excess of flash silica gel 40-63 μm from Aldrich. Fractions were analyzed by TLC using TLC silica gel F254 250 μm precoated-plates from Merck and permanganate stain was used for UV-inactive compounds.

ESI mass spectrometry analysis was performed using a Synapt G2 HDMS instrument, or Agilent 6220 TOF LC/MS with Agilent 1200 HPLC with multi-mode (combined ESI and APCI).

General Reaction Procedure

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4'-Bromoacetophenone (39.8 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with a compressed air gas tube for cooling (FIG. 1). After the time specified in the reaction schemes, the reaction mixture was washed with water and extracted with EtOAc. Purification of the crude product by flash chromatography on silica gel using the indicated solvent system afforded the desired product.

Control Experiment with Base of Different Purities

Four reactions were performed in parallel (DMSO, 25° C., p-Toluenethiol, 1.5 eq Base, 0.2 mmol scale): a) $Cs_2CO_3$ (Aldrich, 99.995% trace metal basis), b) $K_2CO_3$ (Aldrich, 99.995%), c) $Cs_2CO_3$ (Alfa-Aesar, 99.994%), and d) $K_2CO_3$ (Alfa-Aesar, 99.997%). The reactions were monitored by NMR and no appreciable differences in conversion and selectivity in these four reactions was observed.

Time-Dependent Density Functional Theory Calculations

All calculations were performed using computational chemistry software package Gaussian 09 ver. D01. Computational resources were provided by XSEDE—Comet supercomputer.

Ground state geometry of the thiolate-aryl halide EDA complex was optimized at the rM06/6-31+G(d,p)/CPCM-DMSO level of theory. Using this geometry, single point time-dependent density functional theory (TD-DFT) calculation was then performed using the rCAM-B3LYP/6-31+G(d,p)/CPCM-DMSO level of theory. The first 10 excited states of the EDA complex (composed of species 1a and the deprotonated 2a) are reported below. Dominant UV-vis absorption peaks with significant and relevant oscillator strengths (f value) were observed in Excited States 1 and 5.

```
Excited State 1:    Singlet-?Sym 3.2359 eV 383.15 nm f = 0.0364 <S**2> = 0.000
  82 → 83              0.70082 ($\pi_{HOMO}$-$\pi_{LUMO}$, 2*(0.70082)^2*100 = 98% contribution)
Excited state symmetry could not be determined.
Excited State 2:    Singlet-?Sym 4.0543 eV 305.81 nm f = 0.0001 <S**2> = 0.000
  81 → 83              0.68847
Excited state symmetry could not be determined.
Excited State 3:    Singlet-?Sym 4.0754 eV 304.23 nm f = 0.0001 <S**2> = 0.000
  76 → 83              0.65280
  76 → 91              0.11507
Excited state symmetry could not be determined.
Excited State 4:    Singlet-?Sym 4.2165 eV 294.04 nm f = 0.0216 <S**2> = 0.000
  82 → 84              0.52518
  82 → 87              0.14545
  82 → 89              0.41827
Excited state symmetry could not be determined.
```

-continued

| | |
|---|---|
| Excited State 5: | Singlet-?Sym 4.3896 eV 282.45 nm f = 0.1373 <S**2> = 0.000 |
| 82 → 85 | 0.20104 |
| 82 → 86 | 0.20812 |
| 82 → 87 | 0.41952 ($\pi_{HOMO}$-$\pi_{LUMO+4}$, 2*(0.41952)^2*100 = 35% contribution) |
| 82 → 88 | 0.39804 ($\pi_{HOMO}$-$\pi_{LUMO+5}$, 2*(0.39804)^2*100 = 32% contribution) |
| 82 → 89 | −0.12413 |
| 82 → 92 | 0.13025 |
| Excited state symmetry could not be determined. | |
| Excited State 6: | Singlet-?Sym 4.5069 eV 275.10 nm f = 0.0162 <S**2> = 0.000 |
| 82 → 84 | 0.46663 |
| 82 → 87 | −0.17226 |
| 82 → 89 | −0.46169 |
| Excited state symmetry could not be determined. | |
| Excited State 7: | Singlet-?Sym 4.5838 eV 270.49 nm f = 0.1135 <S**2> = 0.000 |
| 82 → 85 | 0.37118 |
| 82 → 86 | 0.24615 |
| 82 → 87 | −0.26832 |
| 82 → 89 | 0.10525 |
| 82 → 90 | 0.11234 |
| 82 → 91 | 0.24975 |
| 82 → 92 | −0.15793 |
| 82 → 93 | −0.21253 |
| 82 → 95 | 0.10313 |
| Excited state symmetry could not be determined. | |
| Excited State 8: | Singlet-?Sym 4.7694 eV 259.96 nm f = 0.0407 <S**2> = 0.000 |
| 77 → 83 | −0.29954 |
| 79 → 84 | −0.18071 |
| 80 → 83 | 0.54640 |
| 82 → 86 | −0.12367 |
| Excited state symmetry could not be determined. | |
| Excited State 9: | Singlet-?Sym 4.7730 eV 259.76 nm f = 0.0094 <S**2> = 0.000 |
| 80 → 83 | −0.16233 |
| 82 → 85 | 0.38498 |
| 82 → 86 | −0.33730 |
| 82 → 87 | 0.11451 |
| 82 → 92 | −0.27487 |
| 82 → 93 | 0.11525 |
| 82 → 97 | −0.19303 |
| Excited state symmetry could not be determined. | |
| Excited State 10: | Singlet-?Sym 4.8448 eV 255.91 nm f = 0.0646 <S**2> = 0.000 |
| 81 → 84 | 0.16037 |
| 81 → 85 | 0.10830 |
| 81 → 86 | 0.21540 |
| 81 → 87 | 0.40282 |
| 81 → 88 | 0.37849 |
| 81 → 90 | 0.13087 |
| 81 → 92 | 0.20198 |

Example 1

Reaction Optimization Screening

C—S cross-coupling reactions were explored in the presence of base ($Cs_2CO_3$) and photo-irradiation and the absence of any photoredox catalysts. Even in the absence of the organic photoredox catalyst after 1 h of white LED irradiation at room temperature (Table 1, entry 1). Further studies revealed white LED irradiation and base were essential for this transformation (entries 2 and 5), while no conversion was observed in the presence of oxygen (entry 6). Without intending to be limited to any particular theory, these results suggest a radical mechanism involving thiyl and (hetero)aryl radicals formed as a result of visible-light promoted intermolecular charge transfer, which subsequently quenched to yield the C—S cross-coupled product (vide infra).

The effect of base and solvent was also investigated (Table 1). Increasingly higher yield was obtained as $Cs_2CO_3$ loading was increased from 0.0 eq (0%, entry 5) to 1.5 eq (97%, entry 1). $K_2CO_3$, which is much less expensive than $Cs_2CO_3$, is also an excellent base for this transformation (91%, entry 7), although $Na_2CO_3$ gave a much lower yield (24%, entry 8). To eliminate the possibility of trace impurities being responsible for this transformation, other sources of base were tested, including $Cs_2CO_3$ (99.995%) and $K_2CO_3$ (99.997%) and observed similarly high yield (Table 2). DMSO was determined to be the best solvent compared to other polar aprotic solvents (entry 1, 9-11).

TABLE 1

Visible-Light Promoted C—S couplings, Effect of Reaction Parameters[a]

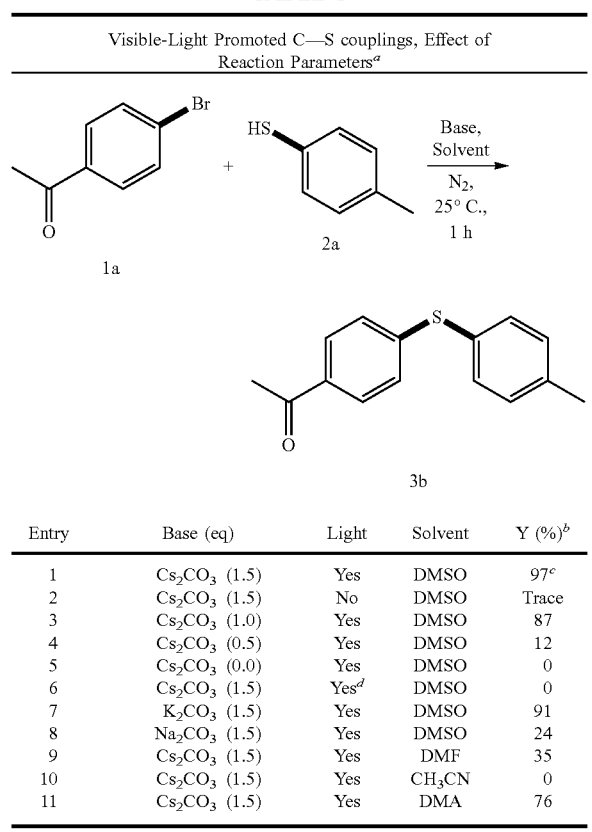

| Entry | Base (eq) | Light | Solvent | Y (%)[b] |
|---|---|---|---|---|
| 1 | Cs₂CO₃ (1.5) | Yes | DMSO | 97[c] |
| 2 | Cs₂CO₃ (1.5) | No | DMSO | Trace |
| 3 | Cs₂CO₃ (1.0) | Yes | DMSO | 87 |
| 4 | Cs₂CO₃ (0.5) | Yes | DMSO | 12 |
| 5 | Cs₂CO₃ (0.0) | Yes | DMSO | 0 |
| 6 | Cs₂CO₃ (1.5) | Yes[d] | DMSO | 0 |
| 7 | K₂CO₃ (1.5) | Yes | DMSO | 91 |
| 8 | Na₂CO₃ (1.5) | Yes | DMSO | 24 |
| 9 | Cs₂CO₃ (1.5) | Yes | DMF | 35 |
| 10 | Cs₂CO₃ (1.5) | Yes | CH₃CN | 0 |
| 11 | Cs₂CO₃ (1.5) | Yes | DMA | 76 |

[a]The beaker with white light emitting diodes (LEDs) was cooled to room temperature with compressed air.
[b]NMR yield using trimethoxybenzene as internal standard.
[c]Isolated yield.
[d]Reaction performed in the presence of air.

TABLE 2

Visible-Light Promoted C—S couplings, Effect of Base Purity

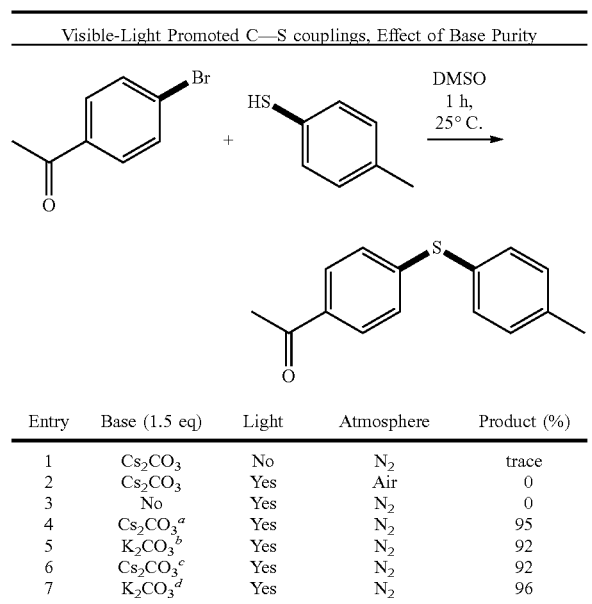

| Entry | Base (1.5 eq) | Light | Atmosphere | Product (%) |
|---|---|---|---|---|
| 1 | Cs₂CO₃ | No | N₂ | trace |
| 2 | Cs₂CO₃ | Yes | Air | 0 |
| 3 | No | Yes | N₂ | 0 |
| 4 | Cs₂CO₃[a] | Yes | N₂ | 95 |
| 5 | K₂CO₃[b] | Yes | N₂ | 92 |
| 6 | Cs₂CO₃[c] | Yes | N₂ | 92 |
| 7 | K₂CO₃[d] | Yes | N₂ | 96 |

[a]Sigma Aldrich 99.995% trace metals basis.
[b]Sigma Aldrich 99.995% trace metals basis.
[c]Alfa Aesar 99.994% trace metals basis.
[d]Alfa Aesar 99.997% trace metals basis.

Additional control reactions were conducted on substrates that could couple through nucleophilic aromatic substitution ($S_NAr$) reactions in the absence of light in order to confirm the role of light in the promotion of these reactions (Scheme 1). No product yield or trace amounts were observed in all cases, demonstrating the importance of irradiation to the reaction.

Scheme 1. Control experiments with subtrates that can couple through a $S_NAr$ reaction.

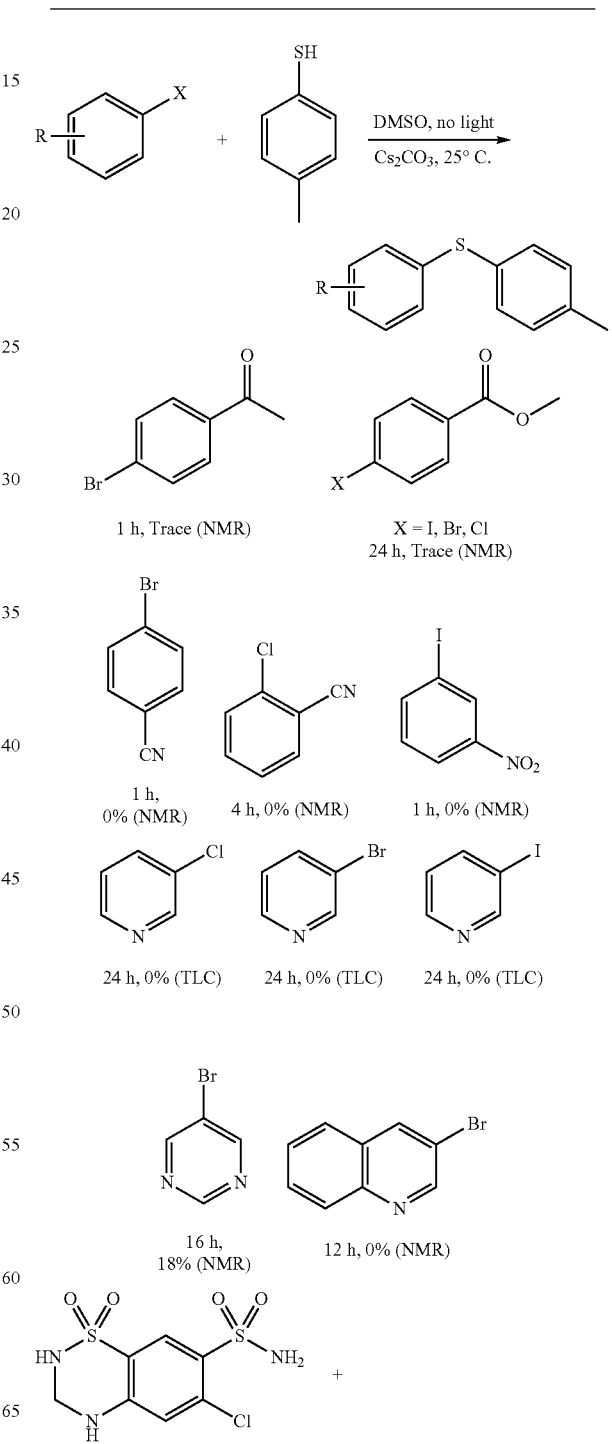

-continued

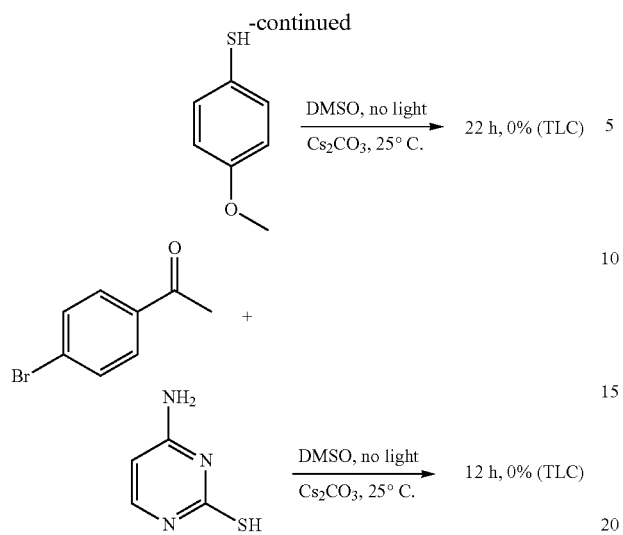

Determined using TLC: Thin Layer Chromatography or NMR: Nuclear Magnetic Resonance

Example 2

Thiol Substrate Scope Screening

Using the optimized conditions determined in Example 1, the scope of the visible-light promoted CS cross-coupling method was further explored. A diverse selection of thiolphenols (2) served as effective cross-coupling partners with 4-bromoacetophenone (1a) to form CS bonds (Scheme 2). C—S coupled products were obtained in good to excellent yield (50-97%) with thiols containing hindered (3c), electron rich (3c-e, h-i, l) and electron-poor (3f-g) functional groups. Alkyl thiols were also successfully coupled (3l). It is worth highlighting that aryl thiol substrates containing free hydroxyl, amine and carboxyl groups were also tolerated under the C—S coupling conditions of the invention (products 3h-j), eliminating the need for protecting groups. To illustrate the robustness and preparative scale utility of this CS cross-coupling method, the production of 3b was scaled up to 50 mmol, while only suffering a small loss in yield (9.71 g, 80%, see Example 8). In addition, 3b was produced in high yield (86%) under sunlight irradiation, demonstrating the potential for sustainable preparation of aromatic thioethers using solar energy (see Example 7).

Scheme 2 Scope of Thiols Synthesized

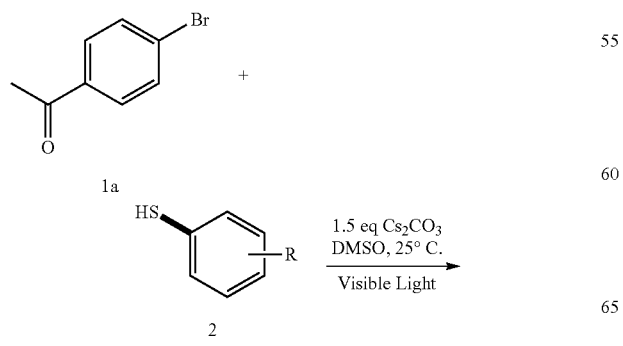

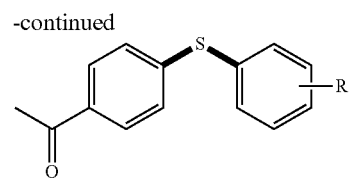
3

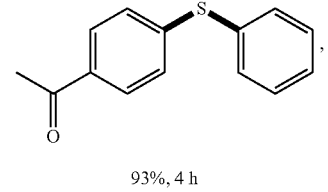
3a

93%, 4 h

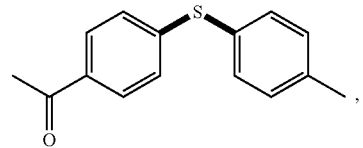
3b

97%, 1 h
80%, 14 h$^a$

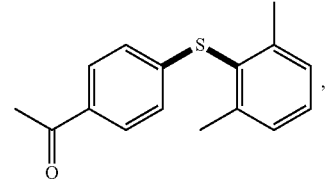
3c

85%, 1 h

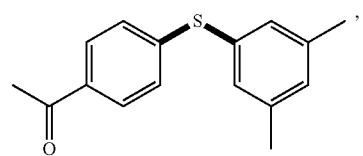
3d

70%, 1 h

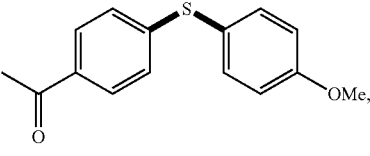
3e

85%, 1 h

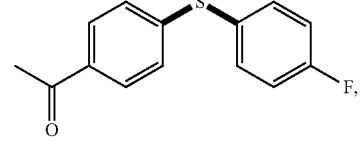
3f

77%, 1 h

-continued

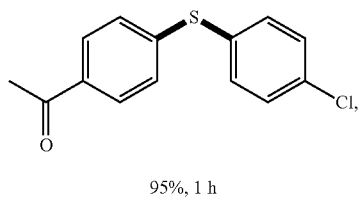

3g

95%, 1 h

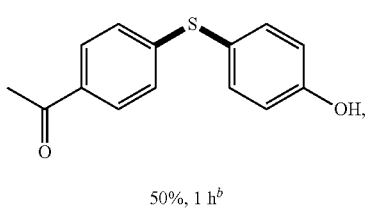

3h

50%, 1 h[b]

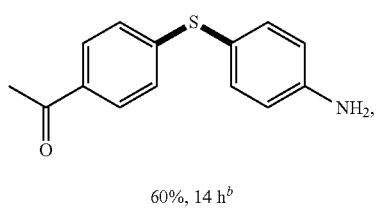

3i

60%, 14 h[b]

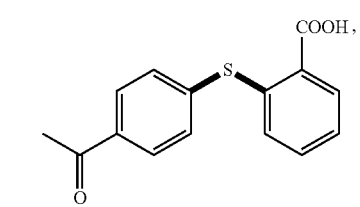

3j

64%, 1 h[b]

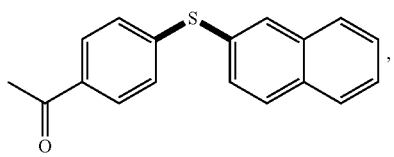

3k

71%, 1.5 h

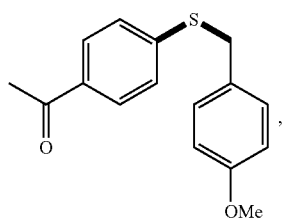

3l

74%, 1 h

General conditions: 1a (0.2 mmol), 2 (1.5 equiv), Cs$_2$CO$_3$ (1.5 equiv), DMSO (1.5 mL), isolated yields provided. [a]50 mmol scale [b]2.0 eq Cs$_2$CO$_3$.

Example 3

Halide Substrate Scope Screening

Various aryl iodides, bromides and chlorides were successfully coupled to thiol nucleophiles (Schemes 3A and 3B). The electronic effects of the aryl iodides resulted in significant differences in reactivity. For example, both longer irradiation times (e.g. 20-24 h) and the use of electron rich thiophenols were required to obtain reasonable yields with electron neutral or rich aryl iodides (4a-f). Conversely, shorter reaction times and higher yields were obtained when electron poor aryl iodides were employed (3b, 4g-o). Aryl bromides also resulted in good reactivity (4j, 1-m, o-v, x). Overall, C—S cross-coupling method of the invention was found to be compatible with aryl halides containing a wide range of functional groups, including ketone (3b, 4g-h, 4l), aldehyde (4i), ester (j), nitro (4k), cyano (4m-n), trifluoromethyl (4o), extended aromatic systems (4p-u), amide (4v-w) and amine groups (4x).

Scheme 3A Scope of C—S
Bond Formations Using ArylChlorides/Bromides/Iodides.

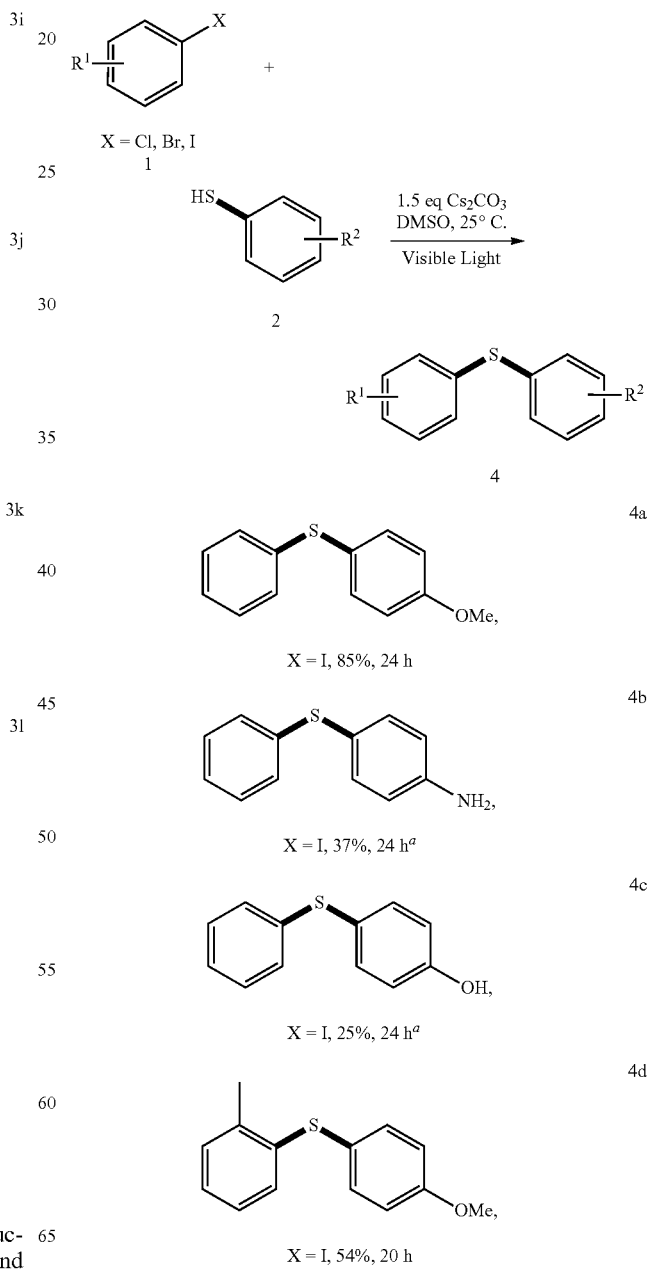

-continued

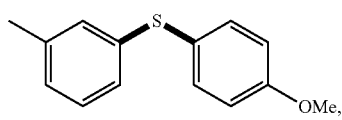

X = I, 72%, 20 h

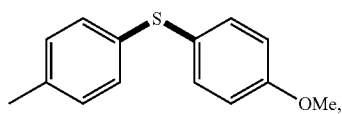

X = I, 79%, 24 h

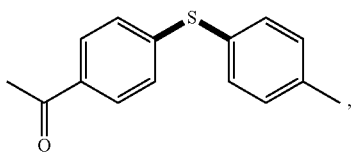

X = I, 89%, 1 h
X = Cl, 95%, 8 h

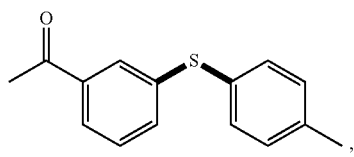

X = I, 89%, 1 h

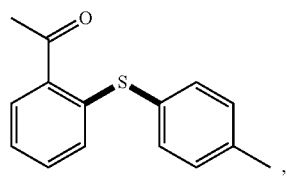

X = I, 76%, 1 h
X = Cl, 82%, 12 h

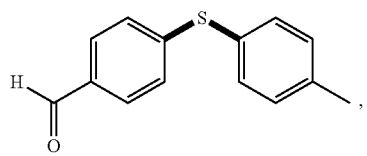

X = I, 87%, 12 h
X = Cl, 78%, 12 h

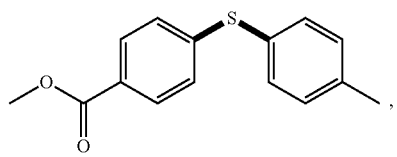

X = Br, 85%, 4 h
X = I, 90%, 4 h
X = Cl, 82%, 12 h

-continued

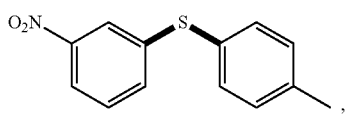

X = I, 80%, 4 h

General conditions: 1 (0.2 mmol), 2 (1.5 equiv), $Cs_2CO_3$ (1.5 equiv), DMSO (1.5 mL), isolated yields provided. [a] 2.0 eq $Cs_2CO_3$.

In comparison to aryl iodides or bromides, aromatic chlorides are more attractive for synthetic applications because they are less expensive and are generally available in great structural diversity. However, aromatic chlorides as cross-coupling partners in photoredox catalyzed thioethers formation are less common. The visible-light promoted arylation of thiols to aryl chloride substrates was then explored. A number of aryl chlorides containing electron-withdrawing groups were successfully coupled to 2a and the corresponding products (3b, 4h-j, 4n, 5i) were isolated in good to excellent yields.

Scheme 3B Scope of C—S
Bond Formations Using ArylChlorides/Bromides/Iodides, Contd.

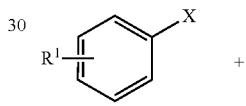

X = Cl, Br, I
1

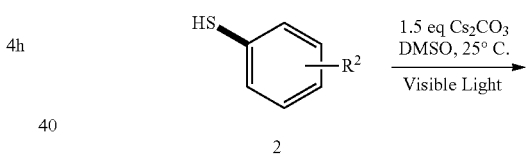

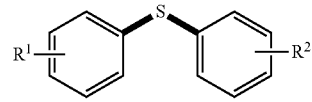

4

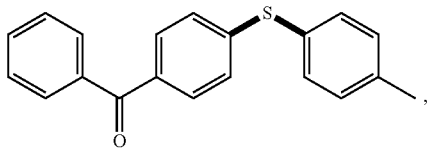

X = Br, 90%, 1 h

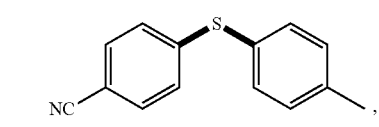

X = Br, 71%, 1 h

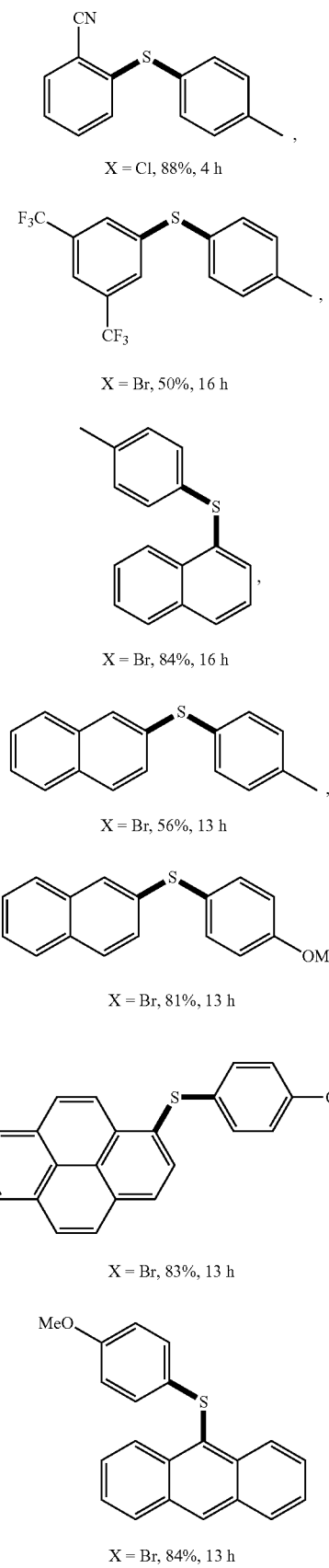

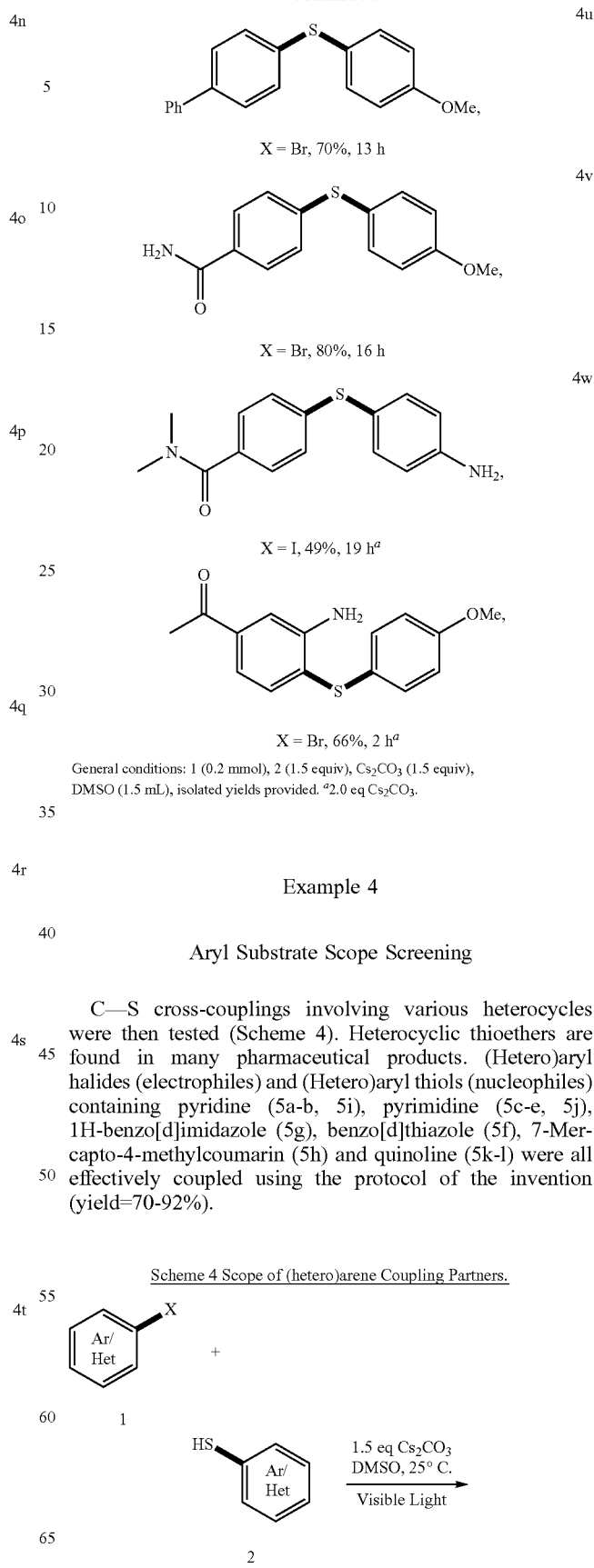

Example 4

Aryl Substrate Scope Screening

C—S cross-couplings involving various heterocycles were then tested (Scheme 4). Heterocyclic thioethers are found in many pharmaceutical products. (Hetero)aryl halides (electrophiles) and (Hetero)aryl thiols (nucleophiles) containing pyridine (5a-b, 5i), pyrimidine (5c-e, 5j), 1H-benzo[d]imidazole (5g), benzo[d]thiazole (5f), 7-Mercapto-4-methylcoumarin (5h) and quinoline (5k-l) were all effectively coupled using the protocol of the invention (yield=70-92%).

-continued

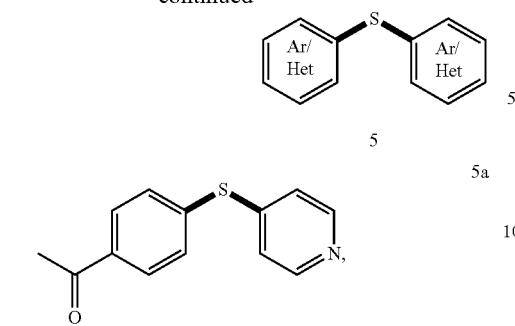

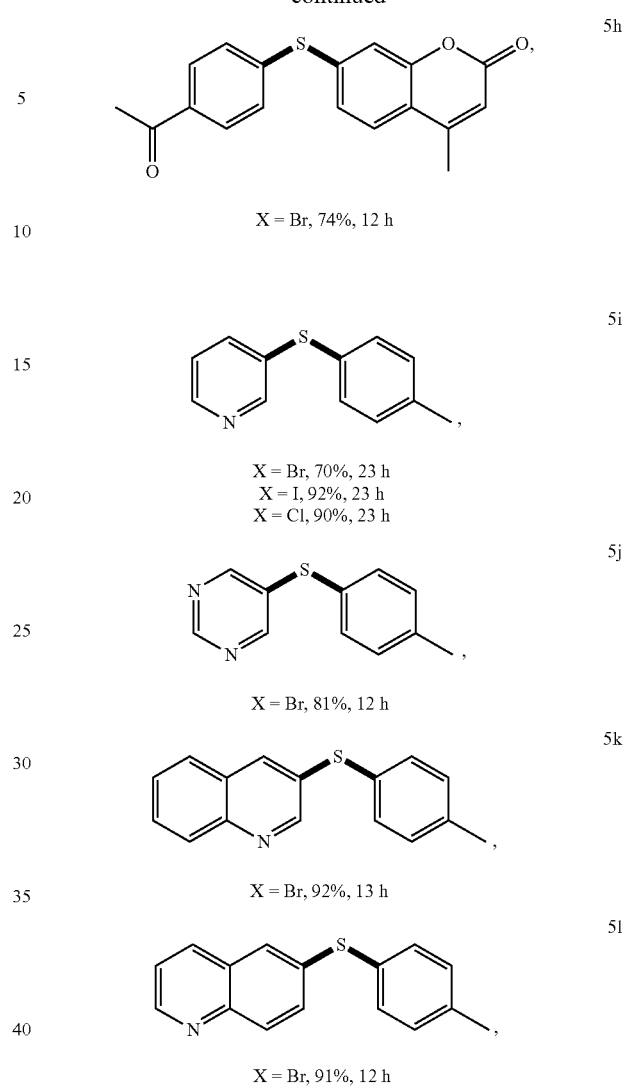

General conditions: 1 (0.2 mmol), 2 (1.5 equiv), Cs$_2$CO$_3$ (1.5 equiv), DMSO (1.5 mL), isolated yields provided. [a]2.0 eq Cs$_2$CO$_3$.

Example 5

Application to Pharmaceutically Relevant Compounds

To demonstrate potential practical applications (Schemes 5-6), the visible-light C—S cross-coupling methodology of the invention was applied to the synthesis of the key structure of 11β-HSD1 inhibitors (6, 80%; 7, 93%). Compared with previously reported methods, the transformation using the methods of the invention involved milder conditions and required less time. Moreover, the method was also evaluated for late-stage functionalization applications. Indometacin, fenofibrate, moclobemide and hydrochlorothiazide pharmaceutical ingredients (all containing an aryl chloride) were subjected to thiophenols under the reaction conditions of the invention and the thiolated compounds 8-13 were obtained in 50%-79% yield.

Scheme 5 Synthetic Applications of the Visible-Light Promoted C—S Bond Formation.
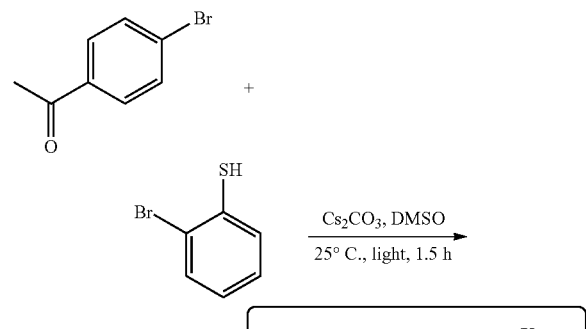
Yield: 84%
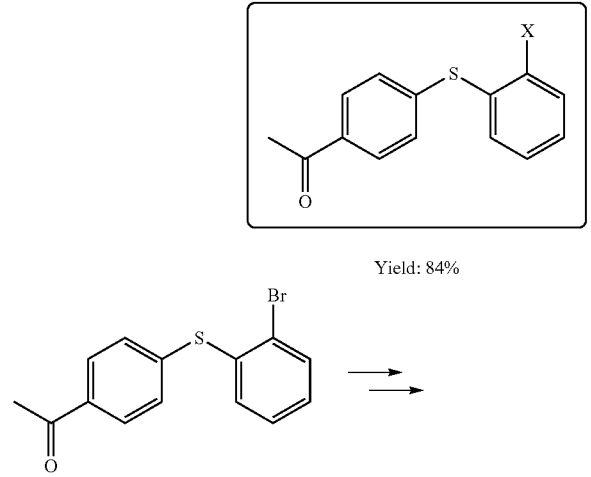
Potent 11β-HSD1 inhibitors
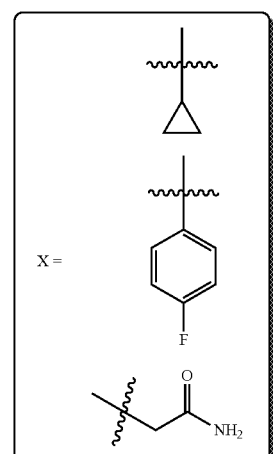
X =
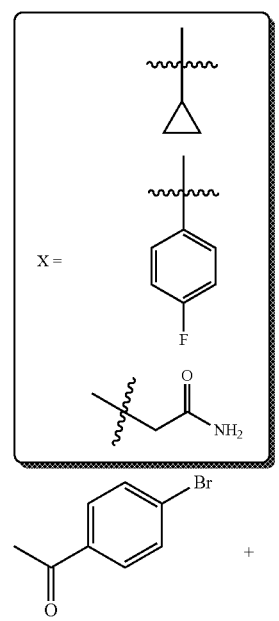
-continued
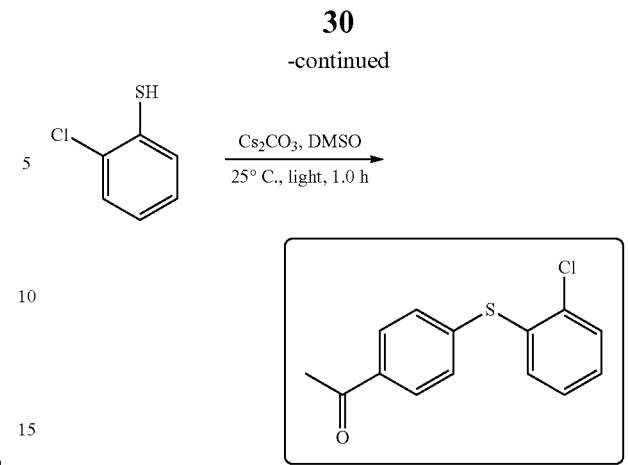
Yield: 93%
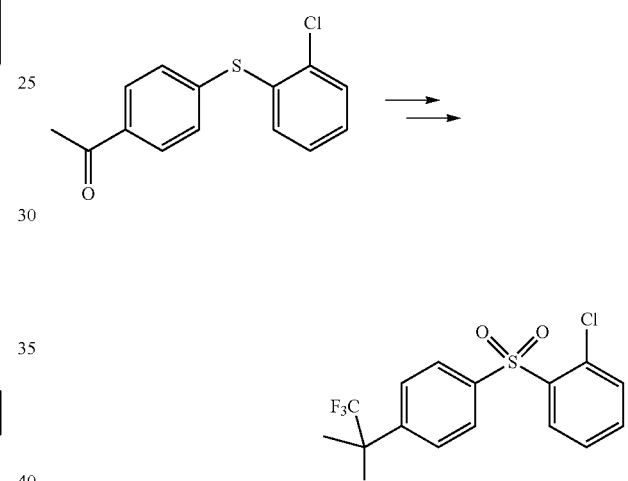
Potent 11β-HSD1 inhibitors
Scheme 6 Synthetic Applications of the Visible-Light Promoted C—S Bond Formation.
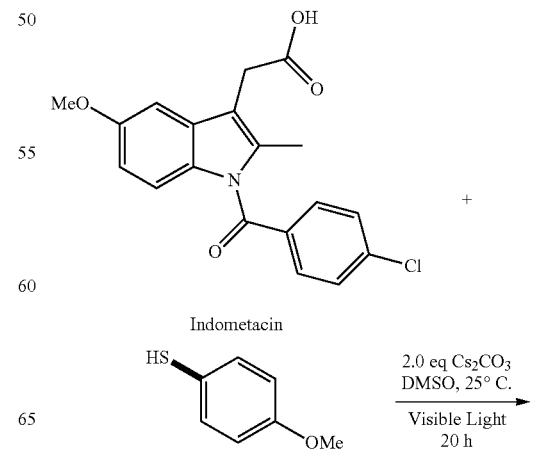

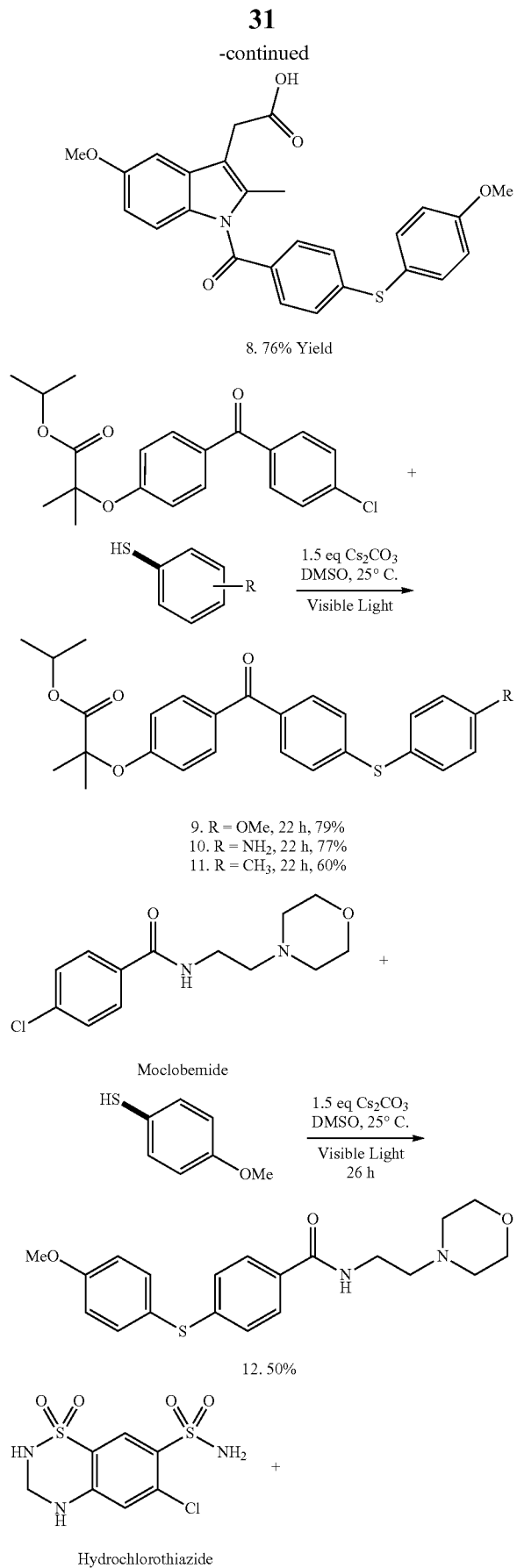
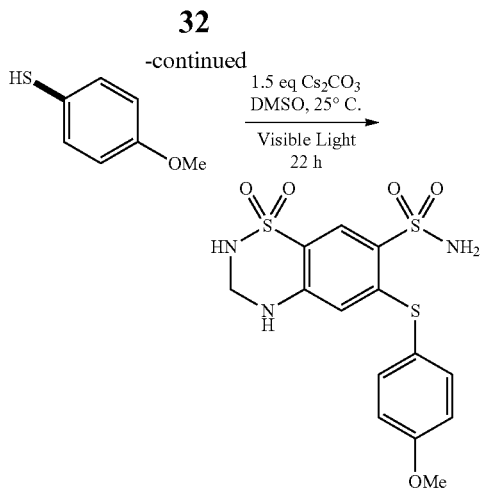

Example 6

Mechanistic Studies

To gain insight into the C—S cross-coupling mechanism, UV-vis spectroscopic measurements were performed on various combinations of 1a, 2a, and $Cs_2CO_3$ in DMSO at $6\times10^{-4}$ M concentration for each species (FIG. 2A). A red-shift in 2a's absorption upon $Cs_2CO_3$ addition was observed, which was attributed to the thiolate anion's absorption (deprotonated 2a) and supported by the up field shift of NMR signal when 2a and $Cs_2CO_3$ were mixed. The formation of a new peak ($\lambda_{max}$=306 nm) was observed when 1a, 2a, and $Cs_2CO_3$ were combined. Without intending to be limited to any particular theory, this peak is proposed to result from the absorption of an electron donoracceptor (EDA) complex, resulting from the association of the thiolate anion and the aryl bromide 1a. At a higher concentration of 0.1 M, a solution containing this EDA complex was visibly yellow and had visible-light absorption tailing to the 400-515 nm region (FIG. 2B).

Density functional theory (DFT) calculations supported the formation of the proposed EDA complex. Based on the calculations, it is proposed that the electron rich thiolate anion (deprotonated 2a) and the electron poor aryl bromide 1a interact via π-π interaction with the closest π-stack distance at ~3.4 Å (FIG. 2D). Additionally, time-dependent DFT calculations computed at the CAM-B3LYP/6-31+G(d, p) level of theory, assigned the observed $\lambda_{max}$=306 nm to have both local and charge transfer excitation characteristics. The peak was predicted to be $\lambda_{calc,1}$=282 nm with an oscillator strength (f value) of 0.137. Specifically, 35% of the 306 nm absorption was contributed by a local excitation involving the thiolate π orbitals ($\pi_{HOMO}-\pi_{LUMO+4}$) while 32% was contributed by a charge transfer excitation from the thiolate to 1a ($\pi_{HOMO}-\pi_{LUMO+5}$). Moreover, time-dependent DFT calculations also predicted a significantly red-shifted peak at 383 nm albeit with weaker absorption (f=0.036). This peak consisted of almost exclusively charge transfer character (98%) involving π orbitals of the thiolate ($\pi_{HOMO}$) and 1a ($\pi_{LUMO}$) and is proposed to be responsible for the observed visible-light absorption.

Based on these analyses, but without intending to be limited to any particular mechanism or theory, it is proposed that the visible-light induced C—S cross-coupling proceeded through the mechanism shown in FIG. 2E. A thiolate anion and a(n) (hetero)aryl halide first associate to form an EDA complex. Due to the charge transfer absorption of this EDA complex, visible-light induced electron transfer from the thiolate anion to the (hetero)aryl halide generates the intermediary halide anion, thiyl and (hetero)aryl radicals; these radicals subsequently couple to yield the desired C—S cross-coupled product.

Example 7

Sunlight-Driven Reactions

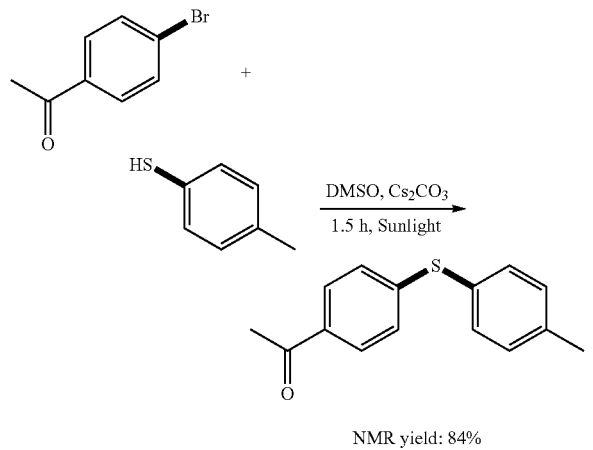

NMR yield: 84%

The reaction was set up in the laboratory according to the general procedure described elsewhere herein, using the $Cs_2CO_3$ (97.7 mg, 0.3 mmol, 1.5 eq.), 4'-Bromoacetophenone (39.8 mg, 0.2 mmol, 1.00 eq.), p-toluenethiol (37.3 mg, 0.3 mmol, 1.5 eq.) and 1.5 mL DMSO. The reaction mixture was evacuated and purged with inert gas ($N_2$) three times. Then, the vial was exposed to natural sunlight irradiation beside a laboratory window from 2:20 PM to 3:50 PM in Boulder Colo., on Apr. 10, 2017, on a partially cloudy day. The $^1$H NMR yield was 84% by using trimethoxybenzene as internal standard.

Example 8

Multi-Gram Scale Experiment

A 100 mL storage flask was charged with a stir bar, flame dried under vacuum and back filled with nitrogen three times. The flask was then charged with $Cs_2CO_3$ (19.54 g, 60 mmol, 1.2 eq.), 4'-Bromoacetophenone (9.95 g, 50 mmol, 1.00 eq.), p-Toluenethiol (7.45 g, 60 mmol, 1.2 eq.) and 60 mL DMSO. The reaction mixture was evacuated and purged with inert gas ($N_2$) three times. The reaction mixture was then placed into an LED-lined beaker and stirred with an air gas tube for cooling. After 14 hours, the reaction mixture was washed with water and extracted with EtOAc three times. Purification of the crude product by flash chromatography on silica gel using the indicated solvent system afforded the desired product (9.710 g, 80%).

Example 9

Compound Characterization 1-(4-(Phenylthio)phenyl)ethan-1-one (3a)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4'-Bromoacetophenone (39.8 mg, 0.2 mmol, 1.00 eq.), benzenethiol (33.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 4 hours, the reaction mixture was washed with water, extracted with EtOA and concentrated in vacuum. The product was isolated by flash chromatography (1:6 EtOAc:hexanes) as white solid (X=Br, 43 mg, 92%).

Physical State: white solid; $R_f$=0.5 (silica gel, 1:6 EtOAc:hexanes); $^1$H NMR (300 MHz, $CDCl_3$) δ 7.84 (dt, J=8.7, 2.1 Hz, 2H), 7.54-7.49 (m, 2H), 7.44-7.41 (m, 3H), 7.23 (dt, J=8.7, 2.1 Hz, 2H), 2.57 (s, 3H); $^{13}$C NMR (75 MHz, $CDCl_3$) δ 197.1, 144.9, 134.5, 133.8, 132.1, 129.7, 128.9, 128.8, 127.5, 26.44; HRMS (ESI-TOF): m/z calcd. for $C_{14}H_{12}OS$ ([M+H]$^+$) 229.0687, found 229.0685.

1-(4-(p-Tolylthio)phenyl)ethan-1-one (3b)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4'-Bromoacetophenone (39.8 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:6 EtOAc:hexanes) as white solid (X=Cl, 95%; X=Br, 47 mg, 97%; X=I, 89%).

Physical State: white solid; $R_f$=0.5 (silica gel, 1:6 EtOAc:hexanes); $^1$H NMR (300 MHz, $CDCl_3$) δ 7.82-7.78 (m, 2H), 7.41 (dt, J=8.1 2.1 Hz, 2H), 7.24-7.21 (m, 2H), 7.18-7.14 (m, 2H), 2.54 (s, 3H), 2.40 (s, 3H); $^{13}$C NMR (75 MHz, $CDCl_3$) δ 197.0, 145.9, 139.3, 134.4, 134.1, 130.5, 128.8, 127.9, 126.6, 26.4, 21.2; HRMS (ESI-TOF): m/z calcd. for $C_{15}H_{14}OS$ ([M+H]+) 243.0844, found 243.0848.

1-(4-((2,6-Dimethylphenyl)thio)phenyl)ethan-1-one (3c)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4'-Bromoacetophenone (39.8 mg, 0.2 mmol, 1.00 eq.), 2,6-dimethylbenzenethiol (41.4 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:6 EtOAc:hexanes) as white solid (X=Br, 44 mg, 85%).

Physical State: white solid; $R_f$=0.5 (silica gel, 1:6 EtOAc:hexanes); $^1$H NMR (300 MHz, CDCl$_3$) δ 7.79 (dt, J=8.7 Hz, 2.1 Hz, 2H), 7.31-7.22 (m, 3H), 6.97 (dt, J=8.7 Hz, 2.1 Hz, 2H), 2.54 (s, 3H), 2.43 (s, 6H); $^{13}$C NMR (75 MHz, CDCl$_3$) δ 197.0, 145.3, 143.9, 133.6, 129.9, 128.9, 128.7, 124.8, 26.4, 21.7; HRMS (ESI-TOF): m/z calcd. for C$_{16}$H$_{16}$OS ([M+H]$^+$) 257.1000, found 257.0998.

1-(4-((3,5-Dimethylphenyl)thio)phenyl)ethan-1-one (3d)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), 3,5-dimethylbenzenethiol (41.4 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:6 EtOAc:hexanes) as white solid (X=Br, 36 mg, 70%).

Physical State: white solid; $R_f$=0.5 (silica gel, 1:6 EtOAc:hexanes); $^1$H NMR (300 MHz, CDCl$_3$) δ 7.83-7.79 (m, 2H), 7.22-7.19 (m, 2H), 7.14-7.13 (m, 2H), 7.02 (dt, J=3.0, 1.1 Hz, 1H), 2.55 (s, 3H), 2.32 (s, 3H), 2.31 (s, 3H); $^{13}$C NMR (75 MHz, CDCl$_3$) δ 197.1, 145.5, 139.4, 134.3, 131.6, 131.2, 130.7, 128.8, 127.2, 26.4, 21.2; HRMS (ESI-TOF): m/z calcd. for C$_{16}$H$_{16}$OS ([M+H]$^+$) 257.1000, found 257.1000.

1-(4-((4-Methoxyphenyl)thio)phenyl)ethan-1-one (3e)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:6 EtOAc:hexanes) as white solid (X=Br, 44 mg, 85%).

Physical State: white solid; $R_f$=0.4 (silica gel, 1:6 EtOAc:hexanes); $^1$H NMR (300 MHz, CDCl$_3$) δ 7.80 (dt, J=8.7 Hz, 2.1 Hz, 2H), 7.49 (dt, J=8.7 Hz, 2.1 Hz, 2H), 7.11 (dt, J=8.7 Hz, 2.1 Hz, 2H), 6.98 (dt, J=8.7 Hz, 2.7 Hz, 2H), 3.87 (s, 3H), 2.55 (s, 3H); $^{13}$C NMR (75 MHz, CDCl$_3$) δ 197.1, 160.7, 146.8, 136.8, 133.9, 128.8, 125.8, 121.4, 115.4, 55.4, 26.4; HRMS (ESI-TOF): m/z calcd. for C$_{15}$H$_{14}$O$_2$S ([M+H]$^+$) 259.0793, found 259.0794.

1-(4-((4-Fluorophenyl)thio)phenyl)ethan-1-one (3f)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), 4-fluorobenzenethiol (38.4 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:6 EtOAc:hexanes) as white solid (X=Br, 38 mg, 77%).

Physical State: white solid; $R_f$=0.5 (silica gel, 1:6 EtOAc:hexanes); $^1$H NMR (300 MHz, CDCl$_3$) δ 7.84-7.79 (m, 2H), 7.54-7.44 (m, 2H), 7.17-7.09 (m, 4H), 2.55 (s, 3H); $^{13}$C NMR (75 MHz, CDCl$_3$) δ 197.0, 163.3 (d, J=248.5 Hz), 145.1, 136.5 (d, J=8.4 Hz), 134.5, 128.9, 126.8, 117.0 (d, J=21.9 Hz), 26.4; HRMS (ESI-TOF): m/z calcd. for C$_{14}$H$_{11}$FOS ([M+H]+) 247.0593, found 247.0594.

1-(4-((4-Chlorophenyl)thio)phenyl)ethan-1-one (3g)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), 4-chlorobenzenethiol (43.2 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:6 EtOAc:hexanes) as white solid (X=Br, 50 mg, 95%).

Physical State: white solid; $R_f$=0.5 (silica gel, 1:6 EtOAc:hexanes); $^1$H NMR (300 MHz, CDCl$_3$) δ 7.85-7.81 (m, 2H), 7.43-7.35 (m, 4H), 7.23-7.20 (m, 2H), 2.56 (s, 3H); $^{13}$C NMR (75 MHz, CDCl$_3$) δ 197.0, 143.9, 134.9, 134.8, 130.94, 129.9, 129.0, 127.8, 26.5; HRMS (ESI-TOF): m/z calcd. for C$_{14}$H$_{11}$ClOS ([M+H]$^+$) 263.0297, found 263.0294.

1-(4-((4-Hydroxyphenyl)thio)phenyl)ethan-1-one (3h)

A 25 mL storage flask was charged with a stir bar, flame dried under vacuum and back filled with nitrogen three times. The flask was then charged with Cs$_2$CO$_3$ (130.3 mg, 0.4 mmol, 2.0 eq.), 4'-Bromoacetophenone (39.8 mg, 0.2 mmol, 1.00 eq.), 4-mercaptophenol (37.8 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:2 EtOAc:hexanes) as white solid (X=Br, 25 mg, 50%).

Physical State: white solid; $R_f$=0.1 (silica gel, 1:6 EtOAc:hexanes); $^1$H NMR (300 MHz, d$_6$-DMSO) δ 10.03 (s, 1H), 7.82 (dt, J=8.7, 2.1 Hz, 2H), 7.39 (dt, J=8.7, 2.6 Hz, 2H), 7.09 (dt, J=8.7, 2.1 Hz, 2H), 6.90 (dt, J=8.7, 2.7 Hz, 2H), 2.50 (s, 3H); $^{13}$C NMR (75 MHz, d$_6$-DMSO) δ 197.3, 159.5, 146.7, 137.4, 134.1, 129.4, 125.7, 118.4, 117.6, 26.9; HRMS (ESI-TOF): m/z calcd. for C$_{14}$H$_{12}$O$_2$S ([M−H]$^-$) 243.0480, found 243.0478.

1-(4-((4-Aminophenyl)thio)phenyl)ethan-1-one (3i)

A 25 mL storage flask was charged with a stir bar, flame dried under vacuum and back filled with nitrogen three times. The flask was then charged with Cs$_2$CO$_3$ (130.3 mg, 0.4 mmol, 2.0 eq.), 4'-Bromoacetophenone (39.8 mg, 0.2 mmol, 1.00 eq.), 4-aminobenzenethiol (37.5 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 14 hours, the reaction mixture was washed with water, extracted with EtOA and concentrated in vacuum. The product was isolated by flash chromatography (1:1 EtOAc:hexanes) as yellow solid (X=Br, 30 mg, 60%).

Physical State: yellow solid; $R_f$=0.4 (silica gel, 1:1 EtOAc:hexanes); $^1$H NMR (300 MHz, $CDCl_3$) δ 7.77 (dt, J=8.7, 2.1 Hz, 2H), 7.33 (dt, J=8.7, 2.4 Hz, 2H), 7.08 (dt, J=8.7, 2.1 Hz, 2H), 6.72 (dt, J=8.7, 2.4 Hz, 2H), 3.91 (s, 2H), 2.53 (s, 3H); $^{13}$C NMR (75 MHz, $CDCl_3$) δ 197.2, 147.9, 147.8, 137.0, 133.6, 128.7, 125.3, 117.7, 116.0, 26.4; HRMS (ESI-TOF): m/z calcd. for $C_{14}H_{13}NOS$ ([M+H]$^+$) 244.0796, found 244.0805.

2-((4-Acetylphenyl)thio)benzoic acid (3j)

A 25 mL storage flask was charged with a stir bar, flame dried under vacuum and back filled with nitrogen three times. The flask was then charged with $Cs_2CO_3$ (130.3 mg, 0.4 mmol, 2.0 eq.), 4'-Bromoacetophenone (39.8 mg, 0.2 mmol, 1.00 eq.), 2-mercaptobenzoic acid (46.2 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (8:1 DCM:MeOH) as white solid (X=Br, 35 mg, 64%).

Physical State: white solid; $R_f$=0.3 (silica gel, 8:1 DCM:MeOH); $^1$H NMR (300 MHz, $d_6$-DMSO) δ 7.99 (dt, J=8.7, 2.1 Hz, 2H), 7.92 (dd, J=7.8, 1.2 Hz, 1H), 7.56 (dt, J=8.4, 2.1 Hz, 2H, 2H), 7.46-7.40 (m, 1H), 7.32 (td, J=7.5, 1.2 Hz, 1H), 6.98 (dd, J=8.0, 0.9 Hz, 1H), 2.60 (s, 3H); $^{13}$C NMR (75 MHz, $d_6$-DMSO) δ 197.7, 167.9, 140.3, 138.6, 136.7, 133.4, 132.9, 131.2, 130.6, 129.9, 129.6, 126.5, 27.2; HRMS (ESI-TOF): m/z calcd. for $C_{15}H_{12}O_3S$ ([M–H]$^+$) 271.0429, found 271.0433.

1-(4-(Naphthalen-2-ylthio)phenyl)ethan-1-one (3k)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4'-Bromoacetophenone (39.8 mg, 0.2 mmol, 1.00 eq.), naphthalene-2-thiol (48.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 1.5 hours, the reaction mixture was washed with water, extracted with EtOA and concentrated in vacuum. The product was isolated by flash chromatography (1:6 EtOAc:hexanes) as white solid (X=Br, 40 mg, 71%).

Physical State: white solid; $R_f$=0.5 (silica gel, 1:6 EtOAc:hexanes); $^1$H NMR (300 MHz, $CDCl_3$) δ 8.04 (t, J=1.2 Hz, 1H), 7.84-7.78 (m, 5H), 7.57-7.48 (m, 3H), 7.28-7.24 (m, 2H), 2.55 (s, 3H); $^{13}$C NMR (75 MHz, $CDCl_3$) δ 197.1, 144.8, 134.6, 133.8, 133.3, 133.0, 130.4, 129.4, 129.3, 128.9, 127.8, 127.7, 127.6, 127.0, 126.9, 26.5; HRMS (ESI-TOF): m/z calcd. for $C_{18}H_{14}OS$ ([M+H]$^+$) 279.0844, found 279.0844.

1-(4-((4-Methoxybenzyl)thio)phenyl)ethan-1-one (3l)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4'-Bromoacetophenone (39.8 mg, 0.2 mmol, 1.00 eq.), (4-methoxyphenyl)methanethiol (46.2 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:5 EtOAc:hexanes) as white solid (X=Br, 40 mg, 74%).

Physical State: white solid; $R_f$=0.5 (silica gel, 1:5 EtOAc:hexanes); $^1$H NMR (300 MHz, $CDCl_3$) δ 7.85 (dt, J=8.7, 2.1 Hz, 2H), 7.35-7.28 (m, 4H), 6.86 (dt, J=8.7, 2.1 Hz, 2H), 4.19 (s, 2H), 3.81 (s, 3H), 2.57 (s, 3H); $^{13}$C NMR (75 MHz, $CDCl_3$) δ 197.1, 159.0, 144.4, 134.1, 129.9, 128.7, 128.0, 126.9, 114.1, 55.3, 36.6, 26.4; HRMS (ESI-TOF): m/z calcd. for $C_{16}H_{16}O_2S$ ([M+H]$^+$) 273.0949, found 273.0947.

(4-Methoxyphenyl)(phenyl)sulfane (4a)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), iodobenzene (40.8 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 24 hours, the reaction mixture was washed with water, extracted with EtOA and concentrated in vacuum. The product was isolated by flash chromatography (1:40 EtOAc:hexanes) as pale yellow oil (X=I, 37 mg, 85%).

Physical State: pale yellow oil; $R_f$=0.4 (silica gel, hexanes); $^1$H NMR (300 MHz, $CDCl_3$) δ 7.49-7.41 (m, 2H), 7.32-7.11 (m, 5H), 6.93 (dt, J=8.7, 2.7 Hz, 2H), 3.85 (s, 3H); $^{13}$C NMR (75 MHz, $CDCl_3$) δ 159.8, 138.6, 135.4, 128.9, 128.2, 125.8, 124.3, 115.0, 55.4; HRMS (ESI-TOF): m/z calcd. for $C_{13}H_{12}OS$ ([M+H]$^+$) 216.0609, found 216.0612.

4-(Phenylthio)phenol (4b)

A 25 mL storage flask was charged with a stir bar, flame dried under vacuum and back filled with nitrogen three times. The flask was then charged with $Cs_2CO_3$ (130.3 mg, 0.4 mmol, 2.0 eq.), iodobenzene (40.8 mg, 0.2 mmol, 1.00 eq.), 4-mercaptophenol (37.8 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 24 hours, the reaction mixture was washed with water, extracted with EtOA and concentrated in vacuum. The product was isolated by flash chromatography (1:1 EtOAc:hexanes) as white solid (X=I, 10 mg, 25%).

Physical State: white solid; $R_f$=0.4 (silica gel, 1:1 EtOAc:hexanes); $^1$H NMR (300 MHz, $CDCl_3$) δ 7.40-7.35 (m, 2H), 7.27-7.12 (m, 5H), 6.86-6.82 (m, 2H), 4.98 (s, 1H); $^{13}$C NMR (75 MHz, $CDCl_3$) δ 155.8, 138.4, 135.5, 128.9, 128.4, 125.9, 124.7, 116.5; HRMS (ESI-TOF): m/z calcd. for $C_{12}H_{10}OS$ ([M]$^+$) 202.0452, found 202.0457.

4-(Phenylthio)aniline (4c)

A 25 mL storage flask was charged with a stir bar, flame dried under vacuum and back filled with nitrogen three times. The flask was then charged with $Cs_2CO_3$ (130.3 mg, 0.4 mmol, 2.0 eq.), iodobenzene (40.8 mg, 0.2 mmol, 1.00 eq.), 4-aminobenzenethiol (37.5 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 24 hours, the reaction mixture was washed with water, extracted with EtOA and concentrated in vacuum. The product was isolated by flash chromatography (1:1 EtOAc:hexanes) as yellow solid (X=I, 15 mg, 37%).

Physical State: yellow solid; $R_f$=0.4 (silica gel, 1:1 EtOAc:hexanes); $^1$H NMR (300 MHz, CDCl$_3$) δ 7.34-7.30 (m, 2H), 7.24-7.19 (m, 2H), 7.15-7.07 (m, 3H), 6.70-6.66 (m, 2H), 3.78 (s, 2H); $^{13}$C NMR (75 MHz, CDCl$_3$) δ 147.0, 139.7, 136.1, 128.8, 127.3, 125.2, 120.5, 115.9; HRMS (ESI-TOF): m/z calcd. for $C_{12}H_{11}NS$ ([M]$^+$) 202.0690, found 202.0691.

(4-Methoxyphenyl)(o-tolyl)sulfane (4d)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 1-iodo-2-methylbenzene (43.6 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 20 hours, the reaction mixture was washed with water, extracted with EtOA and concentrated in vacuum. The product was isolated by flash chromatography (1:40 EtOAc:hexanes) as colorless oil (X=I, 25 mg, 54%).

Physical State: colorless oil; $R_f$=0.4 (silica gel, hexanes); $^1$H NMR (300 MHz, CDCl$_3$) δ 7.36-7.31 (m, 2H), 7.19-7.17 (m, 1H), 7.13-7.03 (m, 2H), 6.99 (dd, J=6.6, 1.8 Hz, 1H), 6.91-6.87 (m, 2H), 3.82 (s, 3H), 2.39 (s, 3H); $^{13}$C NMR (75 MHz, CDCl$_3$) δ 159.5, 137.1, 134.5, 130.2, 129.1, 126.5, 126.1, 124.5, 115.0, 54.4, 20.3; HRMS (ESI-TOF): m/z calcd. for $C_{14}H_{14}OS$ ([M]$^+$) 230.0765, found 230.0772.

(4-Methoxyphenyl)(m-tolyl)sulfane (e)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 1-iodo-3-methylbenzene (43.6 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 20 hours, the reaction mixture was washed with water, extracted with EtOA and concentrated in vacuum. The product was isolated by flash chromatography (1:40 EtOAc:hexanes) as colorless oil (X=I, 33 mg, 72%).

Physical State: colorless oil; $R_f$=0.4 (silica gel, hexanes); $^1$H NMR (300 MHz, CDCl$_3$) δ 7.45-7.42 (m, 2H), 7.16 (t, J=7.6 Hz, 1H), 7.05 (s, 1H), 7.01-6.97 (m, 2H), 6.94-6.91 (m, 2H), 3.85 (s, 3H), 2.31 (s, 3H); $^{13}$C NMR (75 MHz, CDCl$_3$) δ 159.7, 138.8, 138.2, 135.1, 129.0, 128.7, 126.8, 125.5, 124.6, 114.9, 55.4, 21.3; HRMS (ESI-TOF): m/z calcd. for $C_{14}H_{14}OS$ ([M]$^+$) 230.0765, found 230.0769.

(4-Methoxyphenyl)(p-tolyl)sulfane (4f)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 1-iodo-4-methylbenzene (43.6 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 20 hours, the reaction mixture was washed with water, extracted with EtOA and concentrated in vacuum. The product was isolated by flash chromatography (1:40 EtOAc:hexanes) as colorless oil (X=I, 35 mg, 76%).

Physical State: colorless oil; $R_f$=0.4 (silica gel, hexanes); $^1$H NMR (300 MHz, CDCl$_3$) δ 7.37 (dt, J=9.0, 2.7 Hz, 2H), 7.16-7.13 (m, 2H), 7.09-7.05 (m, 2H), 6.91-6.83 (dt, J=9.0, 2.7 Hz, 2H), 3.81 (s, 3H), 2.31 (s, 3H); $^{13}$C NMR (75 MHz, CDCl$_3$) δ 159.5, 136.1, 134.3, 129.8, 129.4, 125.7, 114.9, 55.4, 21.0; HRMS (ESI-TOF): m/z calcd. for $C_{14}H_{14}OS$ ([M+H]$^+$) 230.0765, found 230.0767.

1-(3-(p-Tolylthio)phenyl)ethan-1-one (4g)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 3'-Bromoacetophenone (39.8 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:6 EtOAc:hexanes) as white solid (X=I, 43 mg, 89%).

Physical State: white solid; $R_f$=0.4 (silica gel, 1:6 EtOAc:hexanes); $^1$H NMR (300 MHz, CDCl$_3$) δ 7.83 (td, J=1.8, 0.6 Hz, 1H), 7.75 (dt, J=7.2, 1.6 Hz, 1H), 7.41-7.31 (m, 4H), 7.17 (d, J=7.8 Hz, 2H), 2.54 (s, 3H), 2.36 (s, 3H); $^{13}$C NMR (75 MHz, CDCl$_3$) δ 197.5, 138.8, 138.4, 137.8, 133.5, 132.9, 130.3, 130.0, 129.2, 128.8, 126.0, 26.6, 21.2; HRMS (ESI-TOF): m/z calcd. for $C_{15}H_{14}OS$ ([M+H]$^+$) 243.0844, found 243.0844.

1-(2-(p-Tolylthio)phenyl)ethan-1-one (4h)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 3'-Bromoacetophenone (39.8 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 1 hour (X=I) or 12 hours (X=Cl), the reaction mixture was washed with water, extracted with EtOA and concentrated in vacuum.

The product was isolated by flash chromatography (1:6 EtOAc:hexanes) as white solid (X=Cl, 40 mg, 82%; X=I, 37 mg, 76%).

Physical State: white solid; $R_f$=0.4 (silica gel, 1:6 EtOAc:hexanes); $^1$H NMR (300 MHz, CDCl$_3$) δ 7.82 (dd, J=7.8, 1.5 Hz, 1H), 7.45-7.41 (m, 2H), 7.25-7.20 (m, 3H), 7.14 (td, J=7.8, 1.5 Hz, 1H), 6.87 (dd, J=8.1, 0.9 Hz, 1H), 2.66 (s, 3H), 2.40 (s, 3H); $^{13}$C NMR (75 MHz, CDCl$_3$) δ 199.1, 142.9, 139.2, 135.4, 134.2, 132.0, 131.0, 130.5, 129.4, 127.8, 124.1, 28.2, 21.3; HRMS (ESI-TOF): m/z calcd. for C$_{15}$H$_{14}$OS ([M+H]$^+$) 243.0844, found 243.0847.

4-(p-Tolylthio)benzaldehyde (4i)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4-iodobenzaldehyde (46.4 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 12 hours, the reaction mixture was washed with water, extracted with EtOA and concentrated in vacuum. The product was isolated by flash chromatography (1:6 EtOAc:hexanes) as white solid (X=Cl, 36 mg, 78%; X=I, 40 mg, 87%).

Physical State: white solid; $R_f$=0.4 (silica gel, 1:6 EtOAc:hexanes); $^1$H NMR (300 MHz, CDCl$_3$) δ 9.92 (s, 1H), 7.74-7.70 (m, 2H), 7.45 (dt, J=8.1, 2.1 Hz, 2H), 7.29-7.19 (m, 4H), 2.43 (s, 3H); $^{13}$C NMR (75 MHz, CDCl$_3$) δ 191.2, 148.2, 139.7, 134.8, 133.5, 130.7, 130.1, 127.3, 126.6, 21.3; HRMS (ESI-TOF): m/z calcd. for C$_{14}$H$_{12}$OS ([M+H]$^+$) 229.0687, found 229.0687.

Methyl 4-(p-Tolylthio)benzoate (4j)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), methyl 4-iodobenzoate (52.4 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 4 hours, the reaction mixture was washed with water, extracted with EtOA and concentrated in vacuum. The product was isolated by flash chromatography (1:20 EtOAc:hexanes) as white solid (X=I, 47 mg, 90%, X=Br, 45 mg, 87%, X=Cl, 48 mg, 92%).

Physical State: white solid; $R_f$=0.4 (silica gel, 1:20 EtOAc:hexanes); $^1$H NMR (300 MHz, CDCl$_3$) δ 7.86 (dt, J=9.0, 1.8 Hz, 2H), 7.40 (dt, J=8.1, 1.8 Hz, 2H), 7.23-7.20 (m, 2H), 7.17-7.13 (m, 2H), 3.88 (s, 3H), 2.39 (s, 3H); $^{13}$C NMR (75 MHz, CDCl$_3$) δ 166.7, 145.4, 139.2, 134.3, 130.5, 130.0, 128.2, 127.1, 126.7, 52.0, 21.3; HRMS (ESI-TOF): m/z calcd. for C$_{15}$H$_{14}$O$_2$S ([M+H]$^+$) 259.0793, found 259.0796.

(3-Nitrophenyl)(p-tolyl)sulfane (4k)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 1-iodo-3-nitrobenzene (49.8 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 4 hours, the reaction mixture was washed with water, extracted with EtOA and concentrated in vacuum. The product was isolated by flash chromatography (1:10 EtOAc:hexanes) as yellow solid (X=I, 41 mg, 83%).

Physical State: yellow solid; $R_f$=0.4 (silica gel, 1:20 EtOAc:hexanes); $^1$H NMR (300 MHz, CDCl$_3$) δ 7.97-7.94 (m, 2H), 7.46-7.35 (m, 4H), 7.25-7.22 (m, 2H), 2.40 (s, 3H); $^{13}$C NMR (75 MHz, CDCl$_3$) δ 148.7, 141.6, 139.6, 134.2, 133.3, 130.7, 129.5, 127.9, 122.2, 120.4, 21.3; HRMS (ESI-TOF): m/z calcd. for C$_{13}$H$_{11}$NO$_2$S ([M+H]$^+$) 246.0589, found 246.0588.

Phenyl-(4-(p-tolylthio)phenyl)methanone (4l)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), (4-bromophenyl)(phenyl)methanone (52.2 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:6 EtOAc:hexanes) as white solid (X=Br, 55 mg, 90%).

Physical State: white solid; $R_f$=0.4 (silica gel, 1:5 EtOAc:hexanes); $^1$H NMR (300 MHz, CDCl$_3$) δ 7.77-7.74 (m, 2H), 7.70-7.66 (m, 2H), 7.60-7.54 (m, 1H), 7.50-7.42 (m, 4H), 7.25-7.17 (m, 4H), 2.40 (s, 3H); $^{13}$C NMR (75 MHz, CDCl$_3$) δ 195.7, 145.3, 139.3, 137.7, 134.5, 134.4, 132.2, 130.7, 130.5, 129.8, 128.2, 128.0, 126.5, 21.3; HRMS (ESI-TOF): m/z calcd. for C$_{20}$H$_{16}$OS ([M+H]$^+$) 305.1000, found 305.0998.

4-(p-Tolylthio)benzonitrile (4m)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4-bromobenzonitrile (36.4 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1 hour, the reaction mixture was washed with water, extracted with EtOA and concentrated in vacuum. The product was isolated by flash chromatography (1:10 EtOAc:hexanes) as white solid (X=Br, 32 mg, 71%).

Physical State: white solid; $R_f$=0.5 (silica gel, 1:10 EtOAc:hexanes); $^1$H NMR (300 MHz, CDCl$_3$) δ 7.47-7.39 (m, 4H), 7.28-7.23 (m, 2H), 7.14-7.10 (m, 2H), 2.41 (s, 3H); $^{13}$C NMR (75 MHz, CDCl$_3$) δ 146.6, 139.9, 134.9, 132.3, 130.7, 126.8 126.7, 118.9, 108.3, 21.3; HRMS (ESI-TOF): m/z calcd. for C$_{14}$H$_{11}$NS ([M+H]$^+$) 226.0690, found 226.0692.

2-(p-Tolylthio)benzonitrile (4n)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 2-chlorobenzonitrile (27.4 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 4 hours, the reaction mixture was washed with water, extracted with EtOA and concentrated in vacuum. The product was isolated by flash chromatography (1:7 EtOAc:hexanes) as colorless oil (X=Cl, 40 mg, 88%).

Physical State: white solid; $R_f$=0.5 (silica gel, 1:7 EtOAc:hexanes); $^1$H NMR (300 MHz, $CDCl_3$) δ 7.61 (ddd, J=7.7, 1.5, 0.5 Hz, 1H), 7.42-7.39 (m, 2H), 7.38-7.34 (m, 1H), 7.23-7.18 (m, 2H), 7.04 (ddd, J=8.1, 1.1, 0.5 Hz, 1H), 2.39 (s, 3H); $^{13}$C NMR (75 MHz, $CDCl_3$) δ 143.5, 139.5, 134.3, 133.5, 132.8, 130.6, 128.9, 127.6, 125.9, 117.0, 111.9, 21.3; HRMS (ESI-TOF): m/z calcd. for $C_{14}H_{11}NS$ ($[M+H]^+$) 226.0690, found 226.0694.

(3,5-Bis(trifluoromethyl)phenyl)(p-tolyl)sulfane (4o)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 1-bromo-3,5-bis(trifluoromethyl)benzene (58.6 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 16 hours, the reaction mixture was washed with water, extracted with EtOA and concentrated in vacuum. The product was isolated by flash chromatography (1:40 EtOAc:hexanes) as colorless oil (X=Br, 34 mg, 50%).

Physical State: colorless oil; $R_f$=0.4 (silica gel, hexanes); $^1$H NMR (300 MHz, $CDCl_3$) δ 7.59 (dd, J=1.5, 0.9 Hz, 1H), 7.52-7.51 (m, 2H), 7.43-7.39 (m, 2H), 7.27-7.24 (m, 2H), 2.41 (s, 3H); $^{13}$C NMR (75 MHz, $CDCl_3$) δ 142.6, 140.0, 134.3, 132.3 (q, J=33.1 Hz), 130.9, 128.9, 127.0 (m), 123.0 (q J=270.0 Hz), 119.1(m), 21.3; HRMS (ESI-TOF): m/z calcd. for $C_{15}H_{10}F_6S$ ($[M]^+$) 336.0407, found 336.0403.

Naphthalen-1-yl(p-tolyl)sulfane (4p)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 1-bromonaphthalene (41.4 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 16 hours, the reaction mixture was washed with water, extracted with EtOA and concentrated in vacuum. The product was isolated by flash chromatography (1:40 EtOAc:hexanes) as white solid (X=Br, 42 mg, 84%).

Physical State: white solid; $R_f$=0.4 (silica gel, hexanes); $^1$H NMR (300 MHz, $CDCl_3$) δ 8.43-8.39 (m, 1H), 7.90-7.80 (m, 2H), 7.58-7.50 (m, 3H), 7.43-7.38(m, 1H), 7.22-7.17 (m, 2H), 7.11-7.07 (m, 2H), 2.32 (s, 3H); $^{13}$C NMR (75 MHz, $CDCl_3$) δ 136.6, 134.1, 133.1, 132.7, 132.5, 131.0, 130.3, 130.0, 128.5, 128.4, 126.7, 126.4, 125.8, 125.4, 21.1; HRMS (ESI-TOF): m/z calcd. for $C_{17}H_{14}S$ ($[M]^+$) 250.0816, found 250.0818.

Naphthalen-2-yl(p-tolyl)sulfane (4q)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 2-bromonaphthalene (41.4 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 13 hours, the reaction mixture was washed with water, extracted with EtOA and concentrated in vacuum. The product was isolated by flash chromatography (1:40 EtOAc:hexanes) as white solid (X=Br, 28 mg, 56%).

Physical State: white solid; $R_f$=0.4 (silica gel, hexanes); $^1$H NMR (300 MHz, $CDCl_3$) δ 7.82-7.71 (m, 4H), 7.50-7.43 (m, 2H), 7.40-7.34 (m, 3H), 7.19-7.15 (m, 2H), 2.38 (s, 3H); $^{13}$C NMR (75 MHz, $CDCl_3$) δ 137.6, 134.4, 133.8, 132.1, 132.0, 131.4, 130.1, 128.7, 128.4, 127.9, 127.7, 127.3, 126.5, 125.9, 21.2; HRMS (ESI-TOF): m/z calcd. for $C_{17}H_{14}S$ ($[M]^+$) 250.0816, found 250.0817.

(4-Methoxyphenyl)(naphthalen-2-yl)sulfane (4r)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 1-bromonaphthalene (41.4 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 13 hours, the reaction mixture was washed with water, extracted with EtOA and concentrated in vacuum. The product was isolated by flash chromatography (1:40 EtOAc:hexanes) as white solid (X=Br, 44 mg, 81%).

Physical State: white solid; $R_f$=0.4 (silica gel, hexanes); $^1$H NMR (300 MHz, $CDCl_3$) δ 7.79-7.62 (m, 4H), 7.49-7.39 (m, 4H), 7.31 (dd, J=8.7, 1.8 Hz, 1H), 6.95-6.90 (m, 2H), 3.84 (s, 3H); $^{13}$C NMR (75 MHz, $CDCl_3$) δ 159.9, 135.9, 135.2, 133.8, 131.7, 128.5, 127.7, 127.2, 126.7, 126.5, 126.4, 125.6, 124.4, 115.1, 55.4; HRMS (ESI-TOF): m/z calcd. for $C_{17}H_{14}OS$ ($[M]^+$) 266.0765, found 266.0769.

(4-Methoxyphenyl)(pyren-1-yl)sulfane (4s)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 1-bromopyrene (56.2 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 13 hours, the reaction mixture was washed with water, extracted with EtOA and concentrated in vacuum. The product was isolated by flash chromatography (1:40 EtOAc:hexanes) as yellow solid (X=Br, 57 mg, 83%).

Physical State: yellow solid; $R_f$=0.4 (silica gel, hexanes); $^1$H NMR (300 MHz, $CDCl_3$) δ 8.68 (d, J=9.3 Hz, 1H), 8.23-8.20 (m, 2H), 8.16 (d, J=9.3 Hz, 1H), 8.10-8.01 (m, 4H), 7.92 (d, J=8.1 Hz, 1H), 7.39-7.36 (m, 2H), 6.90-6.87 (m, 2H), 3.81 (s, 3H); $^{13}$C NMR (75 MHz, $CDCl_3$) δ 159.2, 133.2, 132.7, 131.5, 131.4, 131.0, 130.5, 130.4, 129.4, 128.1, 127.5, 127.3, 126.4, 126.2, 125.3, 125.1, 124.5, 124.3, 115.0, 114.6, 55.4; HRMS (ESI-TOF): m/z calcd. for $C_{23}H_{16}OS$ ([M] +) 340.0922, found 340.0926.

Anthracen-9-yl(4-methoxyphenyl)sulfane (4t)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 9-bromoanthracene (51.4 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 13 hours, the reaction mixture was washed with water, extracted with EtOA and concentrated in vacuum. The product was isolated by flash chromatography (1:40 EtOAc: hexanes) as yellow solid (X=Br, 53 mg, 84%).

Physical State: yellow solid; $R_f$=0.4 (silica gel, hexanes); $^1$H NMR (300 MHz, CDCl$_3$) δ 8.91-8.87 (m, 1H), 8.57 (s, 1H), 8.06-8.03 (m, 2H), 7.59-7.48 (m, 4H), 6.99-6.96 (m, 2H), 6.68-6.65 (m, 2H), 3.68 (s, 3H); $^{13}$C NMR (75 MHz, CDCl$_3$) δ 157.7, 134.8, 132.0, 130.0, 129.4, 128.9, 128.5, 127.1, 127.0, 126.9, 125.5, 114.6, 55.2; HRMS (ESI-TOF): m/z calcd. for $C_{21}H_{16}OS$ ([M] +) 316.0922, found 316.0926.

[1,1'-Biphenyl]-4-yl(4-methoxyphenyl)sulfane (4u)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4-bromo-1,1'-biphenyl (46.6 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 13 hours, the reaction mixture was washed with water, extracted with EtOA and concentrated in vacuum. The product was isolated by flash chromatography (1:40 EtOAc: hexanes) as white solid (X=Br, 42 mg, 70%).

Physical State: white solid; $R_f$=0.4 (silica gel, hexanes); $^1$H NMR (300 MHz, CDCl$_3$) δ 7.57-7.54 (m, 2H), 7.50-7.40 (m, 6H), 7.36-7.31 (m, 1H), 7.27-7.23 (m, 2H), 6.96-6.92 (m, 2H), 3.84 (s, 3H); $^{13}$C NMR (75 MHz, CDCl$_3$) δ 159.9, 140.5, 138.8, 137.8, 135.4, 128.8, 128.5, 127.6, 127.3, 126.9, 124.2, 115.1, 55.4; HRMS (ESI-TOF): m/z calcd. for $C_{19}H_{16}OS$ ([M+H]+) 293.1000, found. 293.0995.

4-((4-Methoxyphenyl)thio)benzamide (4v)

A 25 mL storage flask was charged with a stir bar, flame dried under vacuum and back filled with nitrogen three times. The flask was then charged with $Cs_2CO_3$ (195.4 mg, 0.6 mmol, 1.5 eq.), 4-bromobenzamide (80.4.2 mg, 0.4 mmol, 1.00 eq.), 4-methoxybenzenethiol (84.0 mg, 0.6 mmol, 1.5 eq.) and 3.0 mL DMSO. The reaction mixture was evacuated and purged with inert gas ($N_2$) three times. The reaction mixture was then placed into an LED-lined beaker and stirred with an air gas tube for cooling. After stirred for 16 hours, the reaction mixture was washed with water, extracted with EtOA and concentrated in vacuum. The product was isolated by flash chromatography (4:1 EtOAc: hexanes) as white solid (X=Br, 83 mg, 80%).

Physical State: white solid; $R_f$=0.5 (silica gel, 4:1 EtOAc: hexanes); $^1$H NMR (300 MHz, d$_6$-DMSO) δ 7.91 (s, 1H), 7.77 (d, J=8.7 Hz, 2H), 7.48 (d, J=8.9 Hz, 2H), 7.33 (s, 1H), 7.12-7.01 (m, 4H), 3.81 (s, 3H); $^{13}$C NMR (75 MHz, d$_6$-DMSO) δ 167.7, 160.6, 143.0, 136.7, 131.8, 128.7, 126.4, 121.8, 116.1, 55.8; HRMS (ESI-TOF): m/z calcd. for $C_{14}H_{13}NO_2S$ ([M+H]+) 260.0745, found 260.0748.

4-((4-Aminophenyl)thio)-N,N-dimethylbenzamide (4w)

A 25 mL storage flask was charged with a stir bar, flame dried under vacuum and back filled with nitrogen three times. The flask was then charged with $Cs_2CO_3$ (130.3 mg, 0.4 mmol, 2.0 eq.), 4-Iodo-N,N-dimethylbenzamide (55.0 mg, 0.2 mmol, 1.00 eq.), 4-aminobenzenethiol (37.5 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 16 hours, the reaction mixture was washed with water, extracted with EtOA and concentrated in vacuum. The product was isolated by flash chromatography (6:1 EtOAc: hexanes) as white solid (X=I, 27 mg, 49%).

Physical State: white solid; $R_f$=0.4 (silica gel, 6:1 EtOAc: hexanes); $^1$H NMR (300 MHz, CDCl$_3$) δ 7.33-7.26 (m, 4H), 7.10-7.07 (m, 2H), 6.69-6.66 (m, 2H), 3.94 (s, 2H), 3.07 (s, 3H), 2.99 (s, 3H); $^{13}$C NMR (75 MHz, CDCl$_3$) δ 171.3, 147.7, 142.5, 136.6, 132.7, 127.7, 126.1, 118.7, 115.9, 39.6, 35.4; HRMS (ESI-TOF): m/z calcd. for $C_{15}H_{16}N_2OS$ ([M+H]+) 273.1062, found 273.1054.

1-(3-Amino-4-((4-methoxyphenyl)thio)phenyl) ethan-1-one (4x)

A 25 mL storage flask was charged with a stir bar, flame dried under vacuum and back filled with nitrogen three times. The flask was then charged with $Cs_2CO_3$ (130.3 mg, 0.4 mmol, 2.0 eq.), 3'-Amino-4'-bromoacetophenone (42.8 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 2 hours, the reaction mixture was washed with water, extracted with EtOA and concentrated in vacuum. The product was isolated by flash chromatography (1:2 EtOAc:hexanes) as pale yellow oil (X=Br, 36 mg, 66%).

Physical State: pale yellow oil; $R_f$=0.3 (silica gel, 1:2 EtOAc:hexanes); $^1$H NMR (400 MHz, CDCl$_3$) δ 7.28 (d, J=1.6 Hz, 1H), 7.26-7.19 (m, 4H), 6.88-6.77 (m, 2H), 4.27 (s, 2H), 3.77 (s, 3H), 2.52 (s, 3H); $^{13}$C NMR (75 MHz, CDCl$_3$) δ 197.9, 159.3, 146.4, 137.6, 133.5, 132.2, 124.9, 124.2, 118.7, 115.1, 114.3, 55.4), 26.6; HRMS (ESI-TOF): m/z calcd. for $C_{15}H_{15}NO_2S$ ([M+H]+) 274.0902, found 274.0904.

1-(4-(Pyridin-4-ylthio)phenyl)ethan-1-one (5a)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4'-Bromoacetophenone (39.8 mg, 0.2 mmol, 1.00 eq.), pyridine-4-thiol (33.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 14 hours, the reaction mixture was washed with water, extracted with EtOA and concentrated in vacuum. The product was isolated by flash chromatography (3:1 EtOAc: hexanes) as yellow solid (X=Br, 38 mg, 82%).

Physical State: yellow solid; $R_f$=0.4 (silica gel, 3:1 EtOAc:hexanes); $^1$H NMR (300 MHz, CDCl$_3$) δ 8.42 (dd, J=4.5, 1.6 Hz, 2H), 8.00-7.95 (m, 2H), 7.59-7.55 (m, 2H), 7.06 (dd, J=4.5, 1.5 Hz, 2H), 2.62 (s, 3H); $^{13}$C NMR (75 MHz, CDCl$_3$) δ 197.0, 149.9, 147.7, 137.1, 137.0, 133.4, 129.4, 122.4, 26.6; HRMS (ESI-TOF): m/z calcd. for C$_{13}$H$_{11}$NOS ([M+H]$^+$) 230.0640, found 230.0645.

1-(4-(Pyridin-2-ylthio)phenyl)ethan-1-one (5b)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), pyridine-2-thiol (33.3 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1 hours, the reaction mixture was washed with water, extracted with EtOA and concentrated in vacuum. The product was isolated by flash chromatography (3:1 EtOAc:hexanes) as yellow solid (X=Br, 32 mg, 70%).

Physical State: yellow solid; $R_f$=0.4 (silica gel, 3:1 EtOAc:hexanes); $^1$H NMR (300 MHz, CDCl$_3$) δ 8.48 (ddd, J=4.9, 1.9, 0.9 Hz, 1H), 7.96-7.92 (m, 2H), 7.61-7.57 (m, 2H), 7.56-7.52 (m, 1H), 7.15-7.07 (m, 2H), 2.60 (s, 3H); $^{13}$C NMR (75 MHz, CDCl$_3$) δ 197.2, 158.7, 150.1, 138.7, 137.0, 136.5, 132.8, 129.1, 123.5, 121.1, 26.6; HRMS (ESI-TOF): m/z calcd. for C$_{13}$H$_{11}$NOS ([M+H]$^+$) 230.0640, found 230.0645.

1-(4-(Pyrimidin-2-ylthio)phenyl)ethan-1-one (5c)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), pyrimidine-2-thiol (33.6 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 14 hours, the reaction mixture was washed with water, extracted with EtOA and concentrated in vacuum. The product was isolated by flash chromatography (1:1 EtOAc:hexanes) as white solid (X=Br, 35 mg, 76%).

Physical State: white solid; $R_f$=0.1 (silica gel, 1:4 EtOAc:hexanes); $^1$H NMR (300 MHz, CDCl$_3$) δ 8.50 (d, J=4.8 Hz, 2H), 8.02-7.97 (m, 2H), 7.75-7.71 (m, 2H), 7.02 (t, J=4.8 Hz, 1H), 2.62 (s, 3H); $^{13}$C NMR (75 MHz, CDCl$_3$) δ 197.3, 171.7, 157.7, 137.1, 135.7, 134.6, 128.8, 117.5, 26.7; HRMS (ESI-TOF): m/z calcd. for C$_{12}$H$_{10}$N$_2$OS ([M+H]$^+$) 231.0592, found 231.0594.

1-(4-((4-Aminopyrimidin-2-yl)thio)phenyl)ethan-1-one (5d)

A 25 mL storage flask was charged with a stir bar, flame dried under vacuum and back filled with nitrogen three times. The flask was then charged with Cs$_2$CO$_3$ (130.3 mg, 0.4 mmol, 2.0 eq.), 4'-Bromoacetophenone (39.8 mg, 0.2 mmol, 1.00 eq.), 4-aminopyrimidine-2-thiol (38.1 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 12 hours, the reaction mixture was washed with water, extracted with EtOA and concentrated in vacuum. The product was isolated by flash chromatography (3:1 EtOAc:hexanes) as white solid (X=Br, 41 mg, 83%).

Physical State: white solid; $R_f$=0.1 (silica gel, 1:1 EtOAc:hexanes); $^1$H NMR (300 MHz, d$_6$-DMSO) δ 7.98-7.94 (m, 2H), 7.86 (d, J=6.0 Hz, 1H), 7.73-7.69 (m, 2H), 7.03 (s, 2H), 6.20 (d, J=6.7 Hz, 1H), 2.60 (s, 3H); $^{13}$C NMR (75 MHz, d$_6$-DMSO) δ 197.8, 169.1, 163.8, 155.5, 137.1, 136.6, 134.3, 128.9, 102.8, 27.2; HRMS (ESI-TOF): m/z calcd. for C$_{12}$H$_{11}$N$_3$OS ([M+H]$^+$) 246.0701, found 246.0709.

1-(44(4-(Trifluoromethyl)pyrimidin-2-yl)thio)phenyl)ethan-1-one (5e)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), 4-(trifluoromethyl)pyrimidine-2-thiol (54.0 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 22 hours, the reaction mixture was washed with water, extracted with EtOA and concentrated in vacuum. The product was isolated by flash chromatography (1:2 EtOAc:hexanes) as yellow solid (X=Br, 45 mg, 79%).

Physical State: yellow solid; $R_f$=0.2 (silica gel, 1:4 EtOAc:hexanes); $^1$H NMR (300 MHz, CDCl$_3$) δ 8.72 (dd, J=4.8, 0.5 Hz, 1H), 8.03-7.99 (m, 2H), 7.76-7.71 (m, 2H), 7.32 (d, J=5.1 Hz, 1H), 2.64 (s, 3H); $^{13}$C NMR (75 MHz, CDCl$_3$) δ 197.3, 173.2, 159.8, 156.1 (q, J=36.7 Hz), 137.5, 134.7, 134.4, 128.9, 120.0 (q, J=273.7 Hz), 112.8 (q, J=2.6 Hz), 26.7; HRMS (ESI-TOF): m/z calcd. for C$_{13}$H$_9$F$_3$N$_2$OS ([M+H]$^+$) 299.0466, found 299.0458.

1-(4-(Benzo[d]thiazol-2-ylthio)phenyl)ethan-1-one (5f)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), benzo[d]thiazole-2-thiol (40.1 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 21 hours, the reaction mixture was washed with water, extracted with EtOA and concentrated in vacuum. The product was isolated by flash chromatography (1:3 EtOAc:hexanes) as white solid (X=Br, 50 mg, 87%).

Physical State: white solid; $R_f$=0.3 (silica gel, 1:4 EtOAc:hexanes); $^1$H NMR (300 MHz, CDCl$_3$) δ 8.02 (dd, J=8.7, 2.1 Hz, 2H), 7.96-7.93 (m, 1H), 7.79 (dd, J=8.7, 2.1 Hz, 2H), 7.75-7.72 (m, 1H), 7.49-7.43 (m, 1H), 7.37-7.28 (m, 1H), 2.65 (s, 3H); $^{13}$C NMR (75 MHz, CDCl$_3$) δ 197.0, 165.7, 153.6, 137.6, 136.6, 135.9, 133.6, 129.4, 126.4, 124.9, 122.4, 120.9, 26.7; HRMS (ESI-TOF): m/z calcd. for C$_{15}$H$_{11}$NOS$_2$ ([M+H]$^+$) 286.0360, found 286.0363.

1-(4-((1H-benzo[d]imidazol-2-yl)thio)phenyl)ethan-1-one (5g)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4'-Bromoacetophenone (39.8 mg, 0.2 mmol, 1.00 eq.), 1H-benzo[d]imidazole-2-thiol (45.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 12 hours, the reaction mixture was washed with water, extracted with EtOA and concentrated in vacuum. The product was isolated by flash chromatography (1:1 EtOAc:hexanes) as white solid (X=Br, 42 mg, 78%).

Physical State: white solid; $R_f$=0.3 (silica gel, 1:1 EtOAc: hexanes); $^1$H NMR (300 MHz, $CDCl_3$) δ 7.69-7.65 (m, 2H), 7.50 (dd, J=6.0, 3.0 Hz, 2H), 7.39-7.35 (m, 2H), 7.24 (dd, J=6.0, 3.0 Hz, 2H), 2.42 (s, 3H); $^{13}$C NMR (75 MHz, $CDCl_3$) δ 197.1, 145.7, 138.2, 136.0, 130.3, 130.1, 129.1, 128.8, 123.2, 26.5; HRMS (ESI-TOF): m/z calcd. for $C_{15}H_{12}N_2OS$ ([M+H]$^+$) 269.0749, found 269.0746.

7-((4-Acetylphenyl)thio)-4-methyl-2H-chromen-2-one (5h)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 4'-Bromoacetophenone (39.8 mg, 0.2 mmol, 1.00 eq.), 7-mercapto-4-methylcoumarin (57.6 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 12 hours, the reaction mixture was washed with water, extracted with EtOA and concentrated in vacuum. The product was isolated by flash chromatography (1:1 EtOAc:hexanes) as white solid (X=Br, 46 mg, 74%).

Physical State: white solid; $R_f$=0.5 (silica gel, 1:1 EtOAc: hexanes); $^1$H NMR (300 MHz, $CDCl_3$) δ 7.91 (dt, J=8.7, 2.1 Hz, 2H), 7.53 (d, J=8.1 Hz, 1H), 7.44 (dt, J=8.7, 2.1 Hz, 2H), 7.23 (dd, J=8.1, 1.8 Hz, 1H), 7.20 (dd, J=1.8, 0.6 Hz, 1H), 6.25 (q, J=1.2 Hz, 1H), 2.60 (s, 3H), 2.41 (d, J=1.2 Hz, 3H); $^{13}$C NMR (75 MHz, $CDCl_3$) δ 197.0, 160.2, 153.9, 151.8, 140.2, 140.1, 136.3, 131.2, 129.3, 125.9, 125.2, 118.9, 118.1, 115.0, 26.6, 18.6; HRMS (ESI-TOF): m/z calcd. for $C_{18}H_{14}O_3S$ ([M+H]$^+$) 311.0742, found 311.0735.

3-(p-Tolylthio)pyridine (5i)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 3-iodopyridine (40.8 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 23 hours, the reaction mixture was washed with water, extracted with EtOA and concentrated in vacuum. The product was isolated by flash chromatography (1:2 EtOAc:hexanes) as yellow oil (X=Br, 28 mg, 70%, X=I, 38 mg, 92%, X=Cl, 36 mg, 90%).

Physical State: yellow oil; $R_f$=0.4 (silica gel, 1:2=EtOAc: hexanes); $^1$H NMR (300 MHz, $CDCl_3$) δ 8.50 (d, J=1.8 Hz, 1H), 8.41 (dd, J=4.8, 1.2 Hz, 1H), 7.53-7.49 (m, 1H), 7.34-7.30 (m, 2H), 7.19-7.14 (m, 3H), 2.35 (s, 3H); $^{13}$C NMR (75 MHz, $CDCl_3$) δ 150.1, 147.3, 138.4, 136.8, 132.8, 130.3, 129.6, 123.8, 21.2; HRMS (ESI-TOF): m/z calcd. for $C_{12}H_{11}NS$ ([M+H]$^+$) 202.0690, found 202.0696.

5-(p-Tolylthio)pyrimidine (5j)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 5-bromopyrimidine (31.6 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 12 hours, the reaction mixture was washed with water, extracted with EtOA and concentrated in vacuum. The product was isolated by flash chromatography (1:1 EtOAc:hexanes) as yellow solid (X=Br, 33 mg, 81%).

Physical State: yellow solid; $R_f$=0.7 (silica gel, 2:1 EtOAc:hexanes); $^1$H NMR (300 MHz, $CDCl_3$) δ 8.98 (s, 1H), 8.52 (s, 2H), 7.39-7.35 (m, 2H), 7.22-7.19 (m, 2H), 2.37 (s, 3H); $^{13}$C NMR (75 MHz, $CDCl_3$) δ 156.1, 155.8, 139.4, 133.5, 130.7, 127.4, 21.2; HRMS (ESI-TOF): m/z calcd. for $C_{11}H_{10}N_2S$ ([M+H]$^+$) 203.0643, found 203.0646.

3-(p-Tolylthio)quinolone (5k)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 6-bromoquinoline (41.6 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 13 hours, the reaction mixture was washed with water, extracted with EtOA and concentrated in vacuum. The product was isolated by flash chromatography (1:5 EtOAc:hexanes) as colorless oil (X=Br, 52 mg, 92%).

Physical State: yellow oil; $R_f$=0.3 (silica gel, 1:5 EtOAc: hexanes); $^1$H NMR (300 MHz, $CDCl_3$) δ 8.80 (d, J=2.4 Hz, 1H), 8.10-8.06 (m, 1H), 7.99 (dd, J=2.1, 0.6 Hz, 1H), 7.72-7.66 (m, 2H), 7.57-7.51 (m, 1H), 7.39-7.35 (m, 2H), 7.21-7.17 (m, 2H), 2.39 (s, 3H); $^{13}$C NMR (75 MHz, $CDCl_3$) δ 151.5, 146.5, 138.3, 135.6, 132.4, 131.3, 130.4, 129.9, 129.3, 129.2, 128.2, 127.2, 127.1, 21.2; HRMS (ESI-TOF): m/z calcd. for $C_{16}H_{13}NS$ ([M+H]$^+$) 252.0847, found 252.0849.

6-(p-Tolylthio)quinolone (5l)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), 3-bromoquinoline (41.6 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 12 hours, the reaction mixture was washed with water, extracted with EtOA and concentrated in vacuum. The product was isolated by flash chromatography (1:5 EtOAc:hexanes) as yellow oil (X=Br, 46 mg, 91%).

Physical State: yellow oil; $R_f$=0.3 (silica gel, 1:5 EtOAc: hexanes); $^1$H NMR (300 MHz, $CDCl_3$) δ 8.84 (dd, J=4.2, 1.5

Hz, 1H), 8.00-7.96 (m, 1H), 7.60 (d, J=2.1 Hz, 1H), 7.54 (dd, J=8.7, 2.1 Hz, 1H), 7.37-7.33 (m, 2H), 7.37-7.32 (m, 1H), 7.21-7.17 (m, 2H), 2.38 (s, 3H); $^{13}$C NMR (75 MHz, CDCl$_3$) δ 150.1, 147.0, 138.4, 136.5, 135.1, 133.1, 130.6, 130.3, 130.1, 130.0, 128.7, 126.5, 121.6, 21.2; HRMS (ESI-TOF): m/z calcd. for C$_{16}$H$_{13}$NS ([M+H]$^+$) 252.0847, found 252.0851.

1-(4-((2-Bromophenyl)thio)phenyl)ethan-1-one (6)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), 2-bromobenzenethiol (37.8 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1.5 hours, the reaction mixture was washed with water, extracted with EtOA and concentrated in vacuum. The product was isolated by flash chromatography (1:5 EtOAc: hexanes) as white solid (X=Br, 52 mg, 84%).

Physical State: white solid; R$_f$=0.5 (silica gel, 1:4 EtOAc: hexanes); $^1$H NMR (300 MHz, CDCl$_3$) δ 7.92-7.87 (m, 2H), 7.71-7.68 (m, 1H), 7.42-7.38 (m, 1H), 7.34-7.28 (m, 3H), 7.26-7.12 (m, 1H), 2.59 (s, 3H); $^{13}$C NMR (75 MHz, CDCl$_3$) δ 197.1, 142.0 135.3, 134.5, 134.3, 133.7, 129.7, 129.1 129.0, 128.3, 127.4, 26.5; HRMS (ESI-TOF): m/z calcd. for C$_{14}$H$_{11}$BrOS ([M+H]$^+$) 308.9772, found 308.9766.

1-(4-((2-Chlorophenyl)thio)phenyl)ethan-1-one (7)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), 4'-Bromoacetophenone (39.8 mg, 0.2 mmol, 1.00 eq.), 2-bromobenzenethiol (37.8 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 1.5 hours, the reaction mixture was washed with water, extracted with EtOA and concentrated in vacuum. The product was isolated by flash chromatography (1:5 EtOAc: hexanes) as white solid (X=Br, 49 mg, 93%).

Physical State: white solid; R$_f$=0.5 (silica gel, 1:4 EtOAc: hexanes); $^1$H NMR (300 MHz, CDCl$_3$) δ 7.89-7.84 (m, 2H), 7.51-7.48 (m, 1H), 7.42-7.39 (m, 1H), 7.34-7.29(m, 1H), 7.29-7.22 (m, 3H), 2.57 (s, 3H); $^{13}$C NMR (75 MHz, CDCl$_3$) δ 197.1, 142.0, 137.0, 135.2, 134.6, 132.2, 130.4, 129.7, 129.1, 128.8, 127.6, 26.5; HRMS (ESI-TOF): m/z calcd. for C$_{14}$H$_{11}$ClOS ([M+H]$^+$) 263.0297, found 263.0299.

2-(5-Methoxy-1-(44(4-methoxyphenyl)thio)ben-zoyl)-2-methyl-1H-indol-3-yl)acetic acid (8)

A 25 mL storage flask was charged with a stir bar, flame dried under vacuum and back filled with nitrogen three times. The flask was then charged with Cs$_2$CO$_3$ (130.3 mg, 0.4 mmol, 2.0 eq.), Indometacin (71.6 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 20 hours, the reaction mixture was washed with water, extracted with EtOA and concentrated in vacuum. The product was isolated by flash chromatography (10:1 DCM:MeOH) as yellow solid (X=Cl, 70 mg, 76%).

Physical State: yellow solid; R$_f$=0.5 (silica gel, 10:1 DCM:MeOH); $^1$H NMR (300 MHz, CDCl$_3$) δ 7.56-7.48 (m, 4H), 7.11 (dd, J=6.6 Hz, 1.8 Hz, 2H), 6.98-6.90 (m, 4H), 6.67 (dd, J=9.0, 2.7 Hz, 1H), 3.85 (s, 3H), 3.82 (s, 3H), 3.68 (s, 2H), 2.37 (s, 3H); $^{13}$C NMR (75 MHz, CDCl$_3$) δ 177.0, 168.8, 160.8, 155.9, 147.1, 136.9, 136.3 131.6, 131.0, 130.5, 130.3, 125.8, 121.0, 115.5, 115.0, 111.6, 111.2, 101.0, 55.7, 55.4, 30.1, 13.2; HRMS (ESI-TOF): m/z calcd. for C$_{26}$H$_{23}$NO$_5$S ([M+H]+) 462.1375, found 462.1365.

Isopropyl 2-(4-(4-((4-methoxyphenyl)thio)benzoyl) phenoxy)-2-methylpropanoate (9)

A 25 mL storage flask was charged with a stir bar, flame dried under vacuum and back filled with nitrogen three times. The flask was then charged with Cs$_2$CO$_3$ (97.7 mg, 0.3 mmol, 1.5 eq.), Fenofibrate (72.0 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 22 hours, the reaction mixture was washed with water, extracted with EtOA and concentrated in vacuum. The product was isolated by flash chromatography (1:5 EtOAc:hexanes) as white solid (X=Cl, 74 mg, 79%).

Physical State: white solid; R$_f$=0.5 (silica gel, 1:5 EtOAc: hexanes); $^1$H NMR (300 MHz, CDCl$_3$) δ 7.71 (dt, J=9.0, 2.4 Hz, 2H), 7.62 (dt, J=8.7, 1.8 Hz, 2H), 7.49 (dt, J=9.0, 2.4 Hz, 2H), 7.16-7.06 (m, 2H), 7.00-6.92 (m, 2H), 6.91-6.78 (m, 2H), 5.12-5.04 (m, 1H), 3.85 (s, 3H), 1.65 (s, 6H), 1.20 (s, 3H), 1.18 (s, 3H); $^{13}$C NMR (75 MHz, CDCl$_3$) δ 194.5, 173.1, 160.6, 159.4, 145.4, 136.7, 134.7, 131.8, 130.8, 130.4, 125.8, 121.7, 117.2, 115.3, 79.4, 69.3, 55.4, 25.4, 21.5; HRMS (ESI-TOF): m/z calcd. for C$_{27}$H$_{28}$O$_5$S ([M+H]+) 465.1736, found 465.1722.

Isopropyl 2-(4-(4-((4-aminophenyl)thio)benzoyl) phenoxy)-2-methylpropanoate (10)

A 25 mL storage flask was charged with a stir bar, flame dried under vacuum and back filled with nitrogen three times. The flask was then charged with Cs$_2$CO$_3$ (130.3 mg, 0.4 mmol, 2.0 eq.), Fenofibrate (72.0 mg, 0.2 mmol, 1.00 eq.), 4-aminobenzenethiol (37.5 mg, 0.3 mmol, 1.5 eq.) and 1.5 mL DMSO. The reaction mixture was evacuated and purged with inert gas (N$_2$) three times. The reaction mixture was then placed into an LED-lined beaker and stirred with an air gas tube for cooling. After stirred for 22 hours, the reaction mixture was washed with water, extracted with EtOA and concentrated in vacuum. The product was isolated by flash chromatography (1:3 EtOAc:hexanes) as yellow solid (X=Cl, 70 mg, 79%).

Physical State: yellow solid; R$_f$=0.5 (silica gel, 1:2 EtOAc:hexanes); $^1$H NMR (300 MHz, CDCl$_3$) δ 7.73-7.68 (m, 2H), 7.62-7.58 (m, 2H), 7.37-7.32 (m, 2H), 7.12-7.08 (m, 2H), 6.85-6.82 (m, 2H), 6.73-6.69 (m, 2H), 5.12-5.03 (m, 1H), 3.92 (s, 2H), 1.64 (s, 6H), 1.20 (s, 3H), 1.18 (s, 3H); $^{13}$C NMR (75 MHz, CDCl$_3$) δ 194.6, 173.2, 159.3, 147.9, 146.5, 137.0, 134.3, 131.8, 130.9, 130.4, 125.2, 117.9, 117.2, 116.0, 79.4, 69.3, 25.4, 21.5; HRMS (ESI-TOF): m/z calcd. for C$_{26}$H$_{27}$NO$_4$S ([M+H]+) 450.1739, found 450.1750.

Isopropyl 2-methyl-2-(4-(4-(p-tolylthio)benzoyl)phenoxy)propanoate (11)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), Fenofibrate (72.0 mg, 0.2 mmol, 1.00 eq.), p-Toluenethiol (37.3 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 22 hours, the reaction mixture was washed with water, extracted with EtOA and concentrated in vacuum. The product was isolated by flash chromatography (1:6 EtOAc:hexanes) as white solid (X=Cl, 57 mg, 60%).

Physical State: white solid; $R_f$=0.5 (silica gel, 1:6 EtOAc:hexanes); $^1$H NMR (300 MHz, $CDCl_3$) δ 7.74-7.69 (m, 2H), 7.64-7.60 (m, 2H), 7.44-7.40 (m, 2H), 7.24-7.16 (m, 4H), 6.86-6.83 (m, 2H), 5.12-5.04 (m, 1H), 2.39 (s, 3H), 1.65 (s, 6H), 1.21 (s, 3H), 1.18 (s, 3H); $^{13}$C NMR (75 MHz, $CDCl_3$) δ 194.6, 173.1, 159.4, 144.4, 139.2, 135.0, 134.3, 131.8, 130.7, 130.5, 130.4, 128.3, 126.7, 117.2, 79.4, 69.3, 25.4, 21.5, 21.3; HRMS (ESI-TOF): m/z calcd. for $C_{27}H_{28}O_4S$ ([M+H]+) 449.1786, found 449.1775.

4-((4-Methoxyphenyl)thio)-N-(2-morpholinoethyl)benzamide (12)

A 25 mL storage flask was charged with a stir bar, flame dried under vacuum and back filled with nitrogen three times. The flask was then charged with $Cs_2CO_3$ (97.7 mg, 0.3 mmol, 1.5 eq.), Moclobemide (53.7 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 26 hours, the reaction mixture was washed with water, extracted with EtOA and concentrated in vacuum. The product was isolated by flash chromatography (10:1 DCM:MeOH) as white solid (X=Cl, 41 mg, 50%).

Physical State: white solid; $R_f$=0.5 (silica gel, 10:1 DCM:MeOH); $^1$H NMR (300 MHz, $CDCl_3$) δ 7.63 (dd, J=6.9, 2.1 Hz, 2H), 7.48 (dd, J=6.9, 2.1 Hz, 2H), 7.14 (dd, J=6.9, 2.1 Hz, 2H), 6.96 (dd, J=6.9, 2.1 Hz, 2H), 6.73 (s, 1H), 3.87 (s, 3H), 3.73 (t, J=4.5 Hz, 4H), 3.55 (dd, J=11.4, 5.4 Hz, 2H), 2.60 (t, J=6.0 Hz, 2H), 2.51 (t, J=4.5 Hz, 4H); $^{13}$C NMR (75 MHz, $CDCl_3$) δ 166.8, 160.5, 144.1, 136.5, 131.3, 127.4, 126.5, 122.2, 115.3, 66.9, 56.9, 55.4, 53.3, 35.9; HRMS (ESI-TOF): m/z calcd. for $C_{20}H_{24}N_2O_3S$ ([M+H]+) 373.1586, found 373.1578.

6-((4-Methoxyphenyl)thio)-3,4-dihydro-2H-benzo[e][1,2,4]thiadiazine-7-sulfonamide 1,1-dioxide (13)

A 25 mL storage flask was charged with a stir bar, flame dried under vacuum and back filled with nitrogen three times. The flask was then charged with $Cs_2CO_3$ (130.3 mg, 0.4 mmol, 2.0 eq.), Hydrochlorothiazide (59.5 mg, 0.2 mmol, 1.00 eq.), 4-methoxybenzenethiol (42.0 mg, 0.3 mmol, 1.5 eq.) and 1.5 mL DMSO. The reaction mixture was evacuated and purged with inert gas ($N_2$) three times. The reaction mixture was then placed into an LED-lined beaker and stirred with an air gas tube for cooling. After stirred for 22 hours, the reaction mixture was washed with water, extracted with EtOA and concentrated in vacuum. The product was isolated by flash chromatography (10:1 EtOAc:hexane) as white solid (X=Cl, 48 mg, 65%).

Physical State: white solid; $R_f$=0.5 (silica gel, EtOAc); $^1$H NMR (300 MHz, $d_6$-DMSO) δ 7.92 (s, 1H), 7.72 (t, J=7.8 Hz, 2H), 7.50 (dd, J=6.6, 2.1 Hz, 2H), 7.36 (s, 2H), 7.10 (dd, J=6.6, 2.1 Hz, 2H), 6.12 (s, 1H), 4.56 (dd, J=8.1, 2.4 Hz, 2H), 3.83 (s, 3H); $^{13}$C NMR (75 MHz, $d_6$-DMSO) δ 161.1, 146.1, 144.6, 137.8, 127.7, 125.2, 121.1, 117.3, 116.33, 113.5, 55.9, 54.6; HRMS (ESI-TOF): m/z calcd. for $C_{14}H_{15}N_3O_5S_3$ ([M]−) 400.0096, found 400.0099.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of generating an aryl or heteroaryl thioether, the method comprising:
   irradiating a system comprising an aryl or heteroaryl halide, a thiol, dimethyl sulfoxide (DMSO) or dimethyl acetamide (DMA), and at least one base with electromagnetic radiation, and
   forming a carbon-sulfur bond between the aryl or heteroaryl halide and the thiol to provide the aryl or heteroaryl thioether,
   wherein the system is free of transition metal and organic photocatalyst.

2. The method of claim 1, wherein the at least one base is selected from the group consisting of an amine, a phosphine, a carbonate salt, a hydroxide salt, an alkoxide salt, a phosphate salt, a metal hydride, and a carboxylate salt.

3. The method of claim 2, wherein the at least one base is selected from the group consisting of $Na_2CO_3$, $K_2CO_3$, $Rb_2CO_3$, and $Cs_2CO_3$.

4. The method of claim 1, wherein the electromagnetic radiation is selected from the group consisting of UV light, visible light, and natural sunlight.

5. The method of claim 1, wherein the aryl or heteroaryl halide and the thiol are irradiated by a light emitting diode (LED).

6. The method of claim 1, wherein the aryl or heteroaryl halide is at least one selected from the group consisting of fluoride chloride, bromide, and iodide.

7. The method of claim 1, wherein the aryl or heteroaryl halide is optionally substituted with at least one additional substituent selected from the group consisting of $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_8$ cycloalkyl, heterocycloalkyl, $C_1$-$C_6$ alkoxy, aryl, heteroaryl, benzyl, heterocyclyl, cyano, halogen, hydroxy, nitro, $S(C_1$-$C_6$ alkyl), —S(=O)($C_1$-$C_6$ alkyl), —S(=O)$_2$($C_1$-$C_6$ alkyl), —S(=O)$_2$$NH_2$, —S(=O)$_2$NH($C_1$-$C_6$ alkyl), —S(=O)$_2$N($C_1$-$C_6$ alkyl)($C_1$-$C_6$ alkyl), —NHNH$_2$, —NH$_2$, —NH($C_1$-$C_6$ alkyl optionally substituted with 1-2 OH), —N($C_1$-$C_6$ alkyl optionally substituted with 1-2 OH)($C_1$-$C_6$ alkyl optionally substituted with 1-2 OH), —NHC(=O)O($C_1$-$C_6$ alkyl), —N($C_1$-$C_6$ alkyl)C(=O)O($C_1$-$C_6$ alkyl), —($CH_2$)$_n$CHO, —($CH_2$)$_n$C(=O)OH, —($CH_2$)$_n$C(=O)O($C_1$-$C_6$ alkyl), —C(=O)S($C_1$-$C_6$ alkyl), —($CH_2$)$_n$C(=O)NH$_2$, —($CH_2$)$_n$C(=O)NH($C_1$-$C_6$ alkyl), —($CH_2$)$_n$C(=O)N($C_1$-$C_6$ alkyl)($C_1$-$C_6$ alkyl), —($CH_2$)$_n$C(=O)($C_1$-$C_6$ alkyl), —($CH_2$)$_n$C(=O)(aryl), —($CH_2$)$_n$C(=O)(heteroaryl), —(CH$_2$)$_n$C(=O)(heterocyclyl), —(CH$_2$)$_n$OC(=O)O(C$_1$-C$_6$ alkyl), —OC(=O)NH$_2$, —OC(=O)NH(C$_1$-C$_6$ alkyl), —OC(=O)N(C$_1$-C$_6$ alkyl)(C$_1$-C$_6$ alkyl), —(CH$_2$)$_n$NHC(=O)(C$_1$-C$_6$ alkyl), —(CH$_2$)$_n$N(C$_1$-C$_6$ alkyl)C(=O)(C$_1$-C$_6$ alkyl), wherein each occurrence of n is independently an integer ranging from 0-6, and wherein two adjacent substituents on the (hetero)aryl are taken together to form C$_1$-C$_6$ cycloalkylene, C$_1$-C$_6$ heterocycloalkylene, fused aryl, or fused heteroaryl;

wherein each moiety selected from the group consisting of alkyl, —CH$_2$—, alkenyl, alkynyl, heteroalkyl, heteroalkenyl, heteroalkynyl, cycloalkyl, heterocycloalkyl, aryl, heteroaryl, heterocyclyl, benzyl, cycloalkylene, and heterocycloalkylene is independently optionally substituted with at least one selected from the group consisting of C$_1$-C$_6$ alkyl, C$_1$-C$_6$ alkoxy, aryl, heteroaryl, heterocyclyl, OH, halogen, —NH$_2$, —NH(C$_1$-C$_6$ alkyl optionally substituted with 1-2 OH), —N(C$_1$-C$_6$ alkyl optionally substituted with 1-2 OH)(C$_1$-C$_6$ alkyl optionally substituted with 1-2 OH), —C(=O)OH, and —C(=O)(C$_1$-C$_6$ alkyl); or wherein two moieties on the same N atom of the at least additional substituent, or moieties on two different atoms of the at least additional substituent, combine to form C$_3$-C$_8$ heterocyclyl.

8. The method of claim 1, wherein the thiol is selected from the group consisting of optionally substituted C$_1$-C$_6$ alkylthiol, thiophenol, thionaphthol, thioanthracenol, thiophenanthrol, thiopyrenol, benzyl mercaptan, heteroaryl thiol, and heteroarylmethyl thiol.

9. The method of claim 1, wherein the thiol is optionally substituted with at least one additional substituent selected from the group consisting of C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, C$_2$-C$_6$ heteroalkenyl, C$_2$-C$_6$ heteroalkynyl, C$_3$-C$_8$ cycloalkyl, heterocycloalkyl, C$_1$-C$_6$ alkoxy, aryl, heteroaryl, benzyl, heterocyclyl, cyano, halogen, hydroxy, nitro, S(C$_1$-C$_6$ alkyl), —S(=O)(C$_1$-C$_6$ alkyl), —S(=O)$_2$(C$_1$-C$_6$ alkyl), —S(=O)$_2$NH$_2$, —S(=O)$_2$NH(C$_1$-C$_6$ alkyl), —S(=O)$_2$N(C$_1$-C$_6$ alkyl)(C$_1$-C$_6$ alkyl), —NHNH$_2$, —NH$_2$, —NH(C$_1$-C$_6$ alkyl optionally substituted with 1-2 OH), —N(C$_1$-C$_6$ alkyl optionally substituted with 1-2 OH)(C$_1$-C$_6$ alkyl optionally substituted with 1-2 OH), —NHC(=O)O(C$_1$-C$_6$ alkyl), —N(C$_1$-C$_6$ alkyl)C(=O)O(C$_1$-C$_6$ alkyl), —(CH$_2$)$_n$CHO, —(CH$_2$)$_n$C(=O)OH, —(CH$_2$)$_n$C(=O)O(C$_1$-C$_6$ alkyl), —C(=O)S(C$_1$-C$_6$ alkyl), —(CH$_2$)$_n$C(=O)NH$_2$, —(CH$_2$)$_n$C(=O)NH(C$_1$-C$_6$ alkyl), —(CH$_2$)$_n$C(=O)N(C$_1$-C$_6$ alkyl)(C$_1$-C$_6$ alkyl), —(CH$_2$)$_n$C(=O)(C$_1$-C$_6$ alkyl), —(CH$_2$)$_n$C(=O)(aryl), —(CH$_2$)$_n$C(=O)(heteroaryl), —(CH$_2$)$_n$C(=O)(heterocyclyl), —(CH$_2$)$_n$OC(=O)O(C$_1$-C$_6$ alkyl), —OC(=O)NH$_2$, —OC(=O)NH(C$_1$-C$_6$ alkyl), —OC(=O)N(C$_1$-C$_6$ alkyl)(C$_1$-C$_6$ alkyl), —(CH$_2$)$_n$NHC(=O)(C$_1$-C$_6$ alkyl), —(CH$_2$)$_n$N(C$_1$-C$_6$ alkyl)C(=O)(C$_1$-C$_6$ alkyl), wherein each occurrence of n is independently an integer ranging from 0-6, and wherein two adjacent substituents on the thiol are taken together to form C$_1$-C$_6$ cycloalkylene, C$_1$-C$_6$ heterocycloalkylene, fused aryl, or fused heteroaryl;

wherein each moiety selected from the group consisting of alkyl, —CH$_2$—, alkenyl, alkynyl, heteroalkyl, heteroalkenyl, heteroalkynyl, cycloalkyl, heterocycloalkyl, aryl, heteroaryl, heterocyclyl, benzyl, cycloalkylene, and heterocycloalkylene is independently optionally substituted with at least one selected from the group consisting of C$_1$-C$_6$ alkyl, C$_1$-C$_6$ alkoxy, aryl, heteroaryl, heterocyclyl, OH, halogen, —NH$_2$, —NH(C$_1$-C$_6$ alkyl optionally substituted with 1-2 OH), —N(C$_1$-C$_6$ alkyl optionally substituted with 1-2 OH)(C$_1$-C$_6$ alkyl optionally substituted with 1-2 OH), —C(=O)OH, and —C(=O)(C$_1$-C$_6$ alkyl); or wherein two moieties on the same N atom of the at least additional substituent, or moieties on two different atoms of the at least additional substituent, combine to form C$_3$-C$_8$ heterocyclyl.

10. The method of claim 1, wherein the aryl or heteroaryl thioether comprises a first monovalent moiety and a second divalent moiety coupled to a —S— divalent group, wherein the first monovalent moiety is selected from the group consisting of phenyl and heteroaryl, and wherein the second monovalent moiety is selected from the group consisting of phenyl, benzyl, heteroaryl, and heteroarylmethyl, each of which is optionally independently substituted.

11. The method of claim 1, wherein the system is under an inert, oxygen-free atmosphere.

12. The method of claim 1, wherein the aryl or heteroaryl thioether comprises a polymer comprising thioether linkages.

13. The method of claim 1, wherein the aryl or heteroaryl thioether is formed in at least 12% yield.

* * * * *